(12) United States Patent
Dorian et al.

(10) Patent No.: US 9,719,063 B2
(45) Date of Patent: Aug. 1, 2017

(54) SYSTEM AND PROCESS FOR SEPARATING A MATERIAL

(71) Applicant: Biomet Biologics, LLC, Warsaw, IN (US)

(72) Inventors: Randel Dorian, San Diego, CA (US); Michael D. Leach, Warsaw, IN (US); Richard W. Storrs, Berkeley, CA (US); Jason Chavarria, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 344 days.

(21) Appl. No.: 14/456,223

(22) Filed: Aug. 11, 2014

(65) Prior Publication Data

US 2014/0349388 A1    Nov. 27, 2014

Related U.S. Application Data

(62) Division of application No. 13/721,978, filed on Dec. 20, 2012, now Pat. No. 8,801,586, which is a division
(Continued)

(51) Int. Cl.
*B01L 3/00* (2006.01)
*C12M 1/00* (2006.01)
(Continued)

(52) U.S. Cl.
CPC .......... *C12M 47/04* (2013.01); *B01L 3/5021* (2013.01); *C12M 47/02* (2013.01); *G01N 1/286* (2013.01);
(Continued)

(58) Field of Classification Search
CPC ... C12M 47/02; B01L 3/5021; B01L 3/50825; B01L 3/5635; B01L 2200/026; B01L 2300/046; G01N 1/286; G01N 1/4077
See application file for complete search history.

(56) References Cited

U.S. PATENT DOCUMENTS

| 280,820 A | 7/1883 | Hickson et al. |
| 593,333 A | 11/1897 | Park |

(Continued)

FOREIGN PATENT DOCUMENTS

| AU | 696278 | 1/1999 |
| BR | 9103724 | 3/1993 |

(Continued)

OTHER PUBLICATIONS

Japanese Office Action mailed Sep. 9, 2014 for Japan Patent Application No. 2012-520742,which claims benefit of PCT/US2010/041942 filed Jul. 14, 2010, which claims benefit of U.S. Appl. No. 12/504,413, filed Jul. 16, 2009.
(Continued)

*Primary Examiner* — David A Reifsnyder
(74) *Attorney, Agent, or Firm* — Schwegman Lundberg & Woessner, P.A.

(57) ABSTRACT

Disclosed is a system to separate, enrich, and/or purify a cellular population from a biological tissue, such as a tissue sample. For example, an adipose tissue sample can be acquired and disrupted. The disrupted tissue sample can then be separated and purified. The separated components can include multipotent, pluripotent, or other cell populations.

22 Claims, 18 Drawing Sheets

Related U.S. Application Data of application No. 12/395,085, filed on Feb. 27, 2009, now Pat. No. 8,337,711.

(60) Provisional application No. 61/032,619, filed on Feb. 29, 2008, provisional application No. 61/078,178, filed on Jul. 3, 2008.

(51) Int. Cl.
  *G01N 1/28* (2006.01)
  *G01N 1/40* (2006.01)

(52) U.S. Cl.
  CPC ........ *G01N 1/4077* (2013.01); *B01L 3/50825* (2013.01); *B01L 3/5635* (2013.01); *B01L 2200/026* (2013.01); *B01L 2300/046* (2013.01)

(56) References Cited

U.S. PATENT DOCUMENTS

| | | |
|---|---|---|
| 1,468,313 A | 9/1923 | Lux |
| 1,593,814 A | 7/1926 | Vogel |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt, Jr. |
| 3,741,400 A | 6/1973 | Dick |
| 3,779,383 A | 12/1973 | Ayres |
| 3,785,549 A | 1/1974 | Latham, Jr. |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi |
| 4,427,650 A | 1/1984 | Stroetmann et al. |
| 4,427,651 A | 1/1984 | Stroetmann et al. |
| 4,442,655 A | 4/1984 | Stroetmann |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,850,952 A | 7/1989 | Figdor et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,909,251 A | 3/1990 | Seelich |

(56) References Cited

U.S. PATENT DOCUMENTS

| | | |
|---|---|---|
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages et al. |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-Fogh et al. |
| 5,484,383 A | 1/1996 | Fitch, Jr. et al. |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |

(56) References Cited

U.S. PATENT DOCUMENTS

| | | |
|---|---|---|
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,853,600 A | 12/1998 | McNeal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,961,210 A | 10/1999 | McCardel et al. |
| 5,980,734 A | 11/1999 | Itoh et al. |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | DiCesare et al. |
| 6,409,528 B1 | 6/2002 | Bodnar |
| 6,410,344 B1 | 6/2002 | Chung et al. |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,623,959 B2 | 9/2003 | Harris |
| 6,629,919 B2 | 10/2003 | Egozy et al. |
| 6,638,503 B2 | 10/2003 | Chitte et al. |
| 6,676,629 B2 | 1/2004 | Andrew et al. |
| 6,716,187 B1 | 4/2004 | Jorgensen et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,764,531 B2 | 7/2004 | Hogan |
| 6,777,231 B1 | 8/2004 | Katz et al. |
| 6,803,022 B2 | 10/2004 | DiCesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,155,288 B2 | 12/2006 | Soykan et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero et al. |
| 7,354,515 B2 | 4/2008 | Coull et al. |
| 7,374,678 B2 | 5/2008 | Leach et al. |
| 7,411,006 B2 | 8/2008 | Shanbrom |
| 7,470,371 B2 | 12/2008 | Dorian et al. |
| 7,531,355 B2 | 5/2009 | Rodriguez et al. |
| 7,553,413 B2 | 6/2009 | Dorian et al. |
| 7,694,828 B2 | 4/2010 | Swift et al. |
| 7,780,860 B2 | 8/2010 | Higgins et al. |
| 7,806,276 B2 | 10/2010 | Leach et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,901,584 B2 | 3/2011 | Dorian et al. |
| 7,914,689 B2 | 3/2011 | Higgins et al. |
| 7,954,646 B2 | 6/2011 | Leach et al. |
| 7,987,995 B2 | 8/2011 | Dorian et al. |
| 7,992,725 B2 | 8/2011 | Leach et al. |
| 8,048,321 B2 | 11/2011 | Leach et al. |
| 8,062,534 B2 | 11/2011 | Higgins et al. |
| 8,067,534 B2 | 11/2011 | Jagota et al. |
| 8,119,013 B2 | 2/2012 | Leach et al. |
| 8,163,184 B2 | 4/2012 | Leach et al. |
| 8,187,477 B2 | 5/2012 | Dorian et al. |
| 8,313,954 B2 | 11/2012 | Leach et al. |

(56) References Cited

U.S. PATENT DOCUMENTS

| | | | |
|---|---|---|---|
| 8,328,024 | B2 | 12/2012 | Leach et al. |
| 8,337,711 | B2 * | 12/2012 | Dorian ............... B01L 3/5021 210/360.1 |
| 8,474,630 | B2 | 7/2013 | Dorian et al. |
| 8,567,609 | B2 | 10/2013 | Landrigan et al. |
| 8,596,470 | B2 | 12/2013 | Leach et al. |
| 8,783,470 | B2 | 7/2014 | Hecker et al. |
| 8,801,586 | B2 * | 8/2014 | Dorian ............... B01L 3/5021 210/120 |
| 8,808,551 | B2 | 8/2014 | Leach et al. |
| 8,950,586 | B2 | 2/2015 | Dorian et al. |
| 8,992,862 | B2 | 3/2015 | Leach et al. |
| 9,011,800 | B2 | 4/2015 | Leach et al. |
| 2001/0009757 | A1 | 7/2001 | Bischof et al. |
| 2002/0032112 | A1 | 3/2002 | Pages |
| 2002/0035820 | A1 | 3/2002 | Farris |
| 2002/0076400 | A1 | 6/2002 | Katz et al. |
| 2002/0082220 | A1 | 6/2002 | Hoemann et al. |
| 2002/0090711 | A1 | 7/2002 | Karlsson |
| 2002/0104808 | A1 | 8/2002 | Blasetti et al. |
| 2002/0114775 | A1 | 8/2002 | Pathak |
| 2002/0161449 | A1 | 10/2002 | Muschler |
| 2002/0169408 | A1 | 11/2002 | Beretta et al. |
| 2002/0172666 | A1 | 11/2002 | Sacchi et al. |
| 2002/0182664 | A1 | 12/2002 | Dolecek et al. |
| 2002/0192632 | A1 | 12/2002 | Hei et al. |
| 2003/0033021 | A1 | 2/2003 | Plouhar et al. |
| 2003/0033022 | A1 | 2/2003 | Plouhar et al. |
| 2003/0050709 | A1 | 3/2003 | Noth et al. |
| 2003/0050710 | A1 | 3/2003 | Petersen et al. |
| 2003/0082152 | A1 | 5/2003 | Hedrick et al. |
| 2003/0185803 | A1 | 10/2003 | Kadiyala et al. |
| 2003/0191429 | A1 | 10/2003 | Andrew et al. |
| 2003/0205538 | A1 | 11/2003 | Dorian et al. |
| 2004/0005246 | A1 | 1/2004 | Efthimiadis et al. |
| 2004/0013575 | A1 | 1/2004 | Stevens et al. |
| 2004/0120942 | A1 | 6/2004 | McGinnis et al. |
| 2004/0171146 | A1 | 9/2004 | Katz et al. |
| 2004/0182395 | A1 | 9/2004 | Brookman |
| 2004/0182788 | A1 | 9/2004 | Dorian et al. |
| 2004/0182795 | A1 | 9/2004 | Dorian et al. |
| 2004/0251217 | A1 | 12/2004 | Leach et al. |
| 2005/0076396 | A1 | 4/2005 | Katz et al. |
| 2005/0084961 | A1 | 4/2005 | Hedrick et al. |
| 2005/0084962 | A1 | 4/2005 | Simon |
| 2005/0109716 | A1 | 5/2005 | Leach et al. |
| 2005/0130301 | A1 | 6/2005 | McKay et al. |
| 2005/0145187 | A1 | 7/2005 | Gray |
| 2005/0153441 | A1 | 7/2005 | Hedrick et al. |
| 2005/0153442 | A1 | 7/2005 | Katz et al. |
| 2005/0186120 | A1 | 8/2005 | Dorian et al. |
| 2005/0196393 | A1 | 9/2005 | Shanbrom |
| 2005/0196874 | A1 | 9/2005 | Dorian et al. |
| 2005/0247715 | A1 | 11/2005 | Ellsworth et al. |
| 2005/0260174 | A1 | 11/2005 | Fraser et al. |
| 2005/0260175 | A1 | 11/2005 | Hedrick et al. |
| 2005/0282275 | A1 | 12/2005 | Katz et al. |
| 2006/0051865 | A1 | 3/2006 | Higgins et al. |
| 2006/0057693 | A1 | 3/2006 | Simon |
| 2006/0083720 | A1 | 4/2006 | Fraser et al. |
| 2006/0140923 | A1 | 6/2006 | Evangelista et al. |
| 2006/0151384 | A1 | 7/2006 | Ellsworth et al. |
| 2006/0175242 | A1 | 8/2006 | Dorian et al. |
| 2006/0175244 | A1 | 8/2006 | Dorian et al. |
| 2006/0178610 | A1 | 8/2006 | Nowakowski |
| 2006/0196885 | A1 | 9/2006 | Leach et al. |
| 2006/0243676 | A1 | 11/2006 | Swift et al. |
| 2006/0273049 | A1 | 12/2006 | Leach et al. |
| 2006/0273050 | A1 | 12/2006 | Higgins et al. |
| 2006/0278588 | A1 | 12/2006 | Woodell-May |
| 2007/0034579 | A1 | 2/2007 | Dorian et al. |
| 2007/0036768 | A1 | 2/2007 | Fraser et al. |
| 2007/0075016 | A1 | 4/2007 | Leach |
| 2007/0208321 | A1 | 9/2007 | Leach et al. |
| 2008/0011684 | A1 | 1/2008 | Dorian et al. |
| 2008/0164204 | A1 | 7/2008 | Hatamian et al. |
| 2008/0173593 | A1 | 7/2008 | Coull et al. |
| 2008/0193424 | A1 | 8/2008 | McKale et al. |
| 2008/0210645 | A1 | 9/2008 | Coull et al. |
| 2008/0217263 | A1 | 9/2008 | Higgins et al. |
| 2008/0217264 | A1 | 9/2008 | Leach et al. |
| 2008/0217265 | A1 | 9/2008 | Leach et al. |
| 2008/0268064 | A1 | 10/2008 | Woodell-May |
| 2008/0269762 | A1 | 10/2008 | Simon et al. |
| 2008/0283474 | A1 | 11/2008 | Leach et al. |
| 2008/0306431 | A1 | 12/2008 | Yoo |
| 2008/0318317 | A1 | 12/2008 | Roche et al. |
| 2009/0014391 | A1 | 1/2009 | Leach et al. |
| 2009/0018313 | A1 | 1/2009 | Shanbrom |
| 2009/0101599 | A1 | 4/2009 | Dorian et al. |
| 2009/0131827 | A1 | 5/2009 | Crocker et al. |
| 2009/0192528 | A1 | 7/2009 | Higgins et al. |
| 2009/0220482 | A1 | 9/2009 | Higgins et al. |
| 2009/0221075 | A1 | 9/2009 | Dorian et al. |
| 2009/0236297 | A1 | 9/2009 | Dorian et al. |
| 2009/0250413 | A1 | 10/2009 | Hoeppner |
| 2009/0253566 | A1 | 10/2009 | Chavarria |
| 2009/0289014 | A1 | 11/2009 | Hoeppner |
| 2010/0055087 | A1 | 3/2010 | Higgins et al. |
| 2010/0140182 | A1 | 6/2010 | Chapman et al. |
| 2010/0186676 | A1 | 7/2010 | Van Der Berg |
| 2010/0206798 | A1 | 8/2010 | Dorian et al. |
| 2010/0256595 | A1 | 10/2010 | Leach et al. |
| 2010/0323870 | A1 | 12/2010 | Leach et al. |
| 2010/0324450 | A1 | 12/2010 | Leach et al. |
| 2011/0014705 | A1 | 1/2011 | Leach et al. |
| 2011/0020196 | A1 | 1/2011 | Grippi et al. |
| 2011/0021334 | A1 | 1/2011 | Leach et al. |
| 2011/0036786 | A1 | 2/2011 | Ellsworth |
| 2011/0056893 | A1 | 3/2011 | Leach et al. |
| 2011/0065183 | A1 | 3/2011 | Dorian et al. |
| 2011/0077596 | A1 | 3/2011 | Higgins et al. |
| 2011/0168193 | A1 | 7/2011 | Leach et al. |
| 2011/0192804 | A1 | 8/2011 | Landrigan et al. |
| 2011/0251041 | A1 | 10/2011 | Chavarria et al. |
| 2012/0015796 | A1 | 1/2012 | Leach et al. |
| 2014/0051061 | A1 | 2/2014 | Landrigan et al. |
| 2014/0054246 | A1 | 2/2014 | Landrigan et al. |
| 2014/0091048 | A1 | 4/2014 | Leach et al. |
| 2014/0275497 | A1 | 9/2014 | Leach et al. |
| 2014/0356446 | A1 | 12/2014 | Leach et al. |

FOREIGN PATENT DOCUMENTS

| | | |
|---|---|---|
| CA | 1321138 | 8/1993 |
| CA | 2182862 | 6/1996 |
| CA | 2448415 A1 | 12/2002 |
| CN | 1074709 | 7/1993 |
| CN | 1321103 A | 11/2001 |
| CN | 1322146 A | 11/2001 |
| CN | 103702729 A | 4/2014 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 A2 | 11/1987 |
| EP | 0253198 | 1/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1005910 | 6/2000 |
| EP | 1006360 A2 | 6/2000 |
| EP | 1289618 | 3/2003 |
| EP | 1406492 B1 | 4/2004 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |

(56) References Cited

FOREIGN PATENT DOCUMENTS

| | | |
|---|---|---|
| EP | 2558143 A1 | 2/2013 |
| GB | 854715 | 11/1960 |
| JP | 60-053845 | 3/1985 |
| JP | 60250014 A | 12/1985 |
| JP | 2036872 | 2/1990 |
| JP | 02071747 | 3/1990 |
| JP | 2000-189407 A | 7/2000 |
| JP | 2000199760 A | 7/2000 |
| JP | 02129224 | 10/2000 |
| JP | 2004-305439 A | 11/2004 |
| JP | 2005013783 A | 1/2005 |
| JP | 200598704 | 4/2005 |
| JP | 2005098704 | 4/2005 |
| JP | 2005524451 | 8/2005 |
| JP | 2006-305365 A | 11/2006 |
| JP | 2006527025 A | 11/2006 |
| JP | 2008104789 A | 5/2008 |
| JP | 2009-155234 A | 7/2009 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-9617871 A1 | 6/1996 |
| WO | WO-9848938 A1 | 11/1998 |
| WO | WO-0061256 | 10/2000 |
| WO | WO-0074713 A1 | 12/2000 |
| WO | WO-0103756 | 1/2001 |
| WO | WO-0183068 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 | 2/2003 |
| WO | WO-03024215 A1 | 3/2003 |
| WO | WO-03/053362 A2 | 7/2003 |
| WO | WO-03/088905 | 10/2003 |
| WO | WO-03/092894 | 11/2003 |
| WO | WO-03/099412 A1 | 12/2003 |
| WO | WO-2004009207 | 1/2004 |
| WO | WO-2004104553 | 12/2004 |
| WO | WO-2005/034843 A2 | 4/2005 |
| WO | WO-2006041406 A1 | 4/2006 |
| WO | WO-2007127834 A2 | 11/2007 |
| WO | WO-2007142908 A1 | 12/2007 |
| WO | WO-2008127639 A1 | 10/2008 |
| WO | WO-2009021257 A1 | 2/2009 |
| WO | WO-2009111338 A1 | 9/2009 |
| WO | WO-2011008836 A1 | 1/2011 |

OTHER PUBLICATIONS

Chinese Office Action mailed Nov. 21, 2014 for Chinese Patent Application No. 201280030026.X.

International Preliminary Report on Patentability and Written Opinion mailed on Mar. 12, 2015 for PCT/US2013/056793 claiming benefit of U.S. Appl. No. 13/595,461, filed Aug. 27, 2012.

International Search Report and Written Opinion mailed Dec. 5, 2013 for PCT/US2013/056793 claiming benefit of U.S. Appl. No. 13/595,461, filed Aug. 27, 2012.

Preliminary Notice of Reasons for Rejection for Japanese Patent Application No. 2014-024420 mailed on Feb. 24, 2015.

"Caps for Corning® and Costar® Plastic Labware," Technical Bulletin. (Dec. 2008) Corning, Incorporated.

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Centrifuge Tubes" Corning Costar brochure. 1996/1997 Catalog pp. 76-77.

"Clotalyst® Autologous Clotting Factor" brochure. (Aug. 15, 2008) Biomet Biologics.

"Clotalyst® Autologous Clotting Factor. Would you like to have an autologous thrombin for rapid clotting and haemostasis?" Brochure. Biomet Biologics (Aug. 15, 2008).

"Corning® 15 and 50 mL Centrifuge Tubes," Life Sciences. (Jun. 2005) Corning Incorporated.

"Cytori Celution Cell Concentrate Device," Exhibit 14, 510(k) Summary, FDA approval K060482 (Sep. 28, 2006).

"Frequently Asked Questions, 1. Kits, 2. Enzymes," (2003) 3 pages Worthington Biochemical Corp.

"Letter CryoSeal FS System. Vaccines, Blood & Biologics," letter. (Jul. 26, 2007) FDA U.S. Food and Drug Administation. http://www.fda.gov/BiologicsBloodVaccines/BloodBloodProducts/ApprovedProducts/PremarketApprovalsPMAs/ucm091631.htm (Web accessed Aug. 12, 2011).

"MarrowStim™ Concentration Kit Peripheral Arterial Disease (PAD) Study" brochure. Web. Jul. 2, 2009 http://www.biomet.com/patients/clinical_recruitment_padstudy.cfm.

"MarrowStim™ Concentration System," brochure. Biomet Biologics Jun. 15, 2008.

"Plasmax® Plasma Concentration System" brochure. (Jun. 15, 2008) Biomet® Biologics.

"Prosys PRP Kit," brochure Tozai Holdings, Inc. http://tozaiholdings.en.ec21.com/Prosys_PRP_Kit--5467051_5467061.html Printed from Web Aug. 24, 2011.

"Prosys PRP Kit," Tozai Holdings, Inc. EC21 Global B2B Marketplace http://www.ec21.com/product-details/Prosys-PRP-Kit--5467061.html Printed from Web Jul. 18, 2011.

"ThermoGenesis Corp. to Supply Autologous Thrombin Kits to Biomet, Inc.," PR Newslink: http:/tinyurl.com/4h3up. (Apr. 5, 2005) http://www.noblood.org/press-releases/2128-thermogenesis-corp-supply-autologous-thrombin-kits-biomet-inc [web accessed Sep. 27, 2011].

"Trypsinization of Adherent Cells," (undated) 2 pages.

"Trypsinizing cells." Bart's Cookbook, Web. Apr. 14, 2010. http://pingu.salk.edu/~sefton/Hyper_protocols/trypsin.html.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Badiavas, et al., "Treatment of Chronic Wounds With Bone Marrow-Derived Cells," (Reprinted) Arch Dermatol. 139:510-516 (Apr. 2003).

Bang, N.U., et al., "Plasma Protein Requirements for Human Platelet Aggregation" Ann. N.Y. Acad Sci, 201:280-299 (1972).

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." J Trauma 31:3 (1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," J Thorac Cardiovasc Surg 105: 5 (1993): 892-7.

BioCUE™ Platelet Concentration System, Jun. 2010. (2 pages).

Biopolymers, vol. 27, pp. 763-774, 1988, Gerald Marx, "Mechanism of Fibrin Coagulation Based on Selective, Cation-Driven, Protofibral Association".

Boomgaard, et al., "Pooled Platelet Concentrates Prepared by the Platelet-Rich-Plasma Method and Filtered with Three Different Filters and Stored for 8 Days." Vox Sanq, vol. 68: 82-89, Feb. 1995.

Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research (May 2006) pp. 857-866.

(56) References Cited

OTHER PUBLICATIONS

Casali, B., F. Rodeghiero, A. Tosetto, B. Palmieri, R. Immovilli, C. Ghedini, and P. Rivasi "Fibrin glue from single-donation autologous plasmapheresis." Transfusion 32:7 (1992): 641-3.

Chinese Office Action mailed Jun. 30, 2014 for Chinese Patent Application No. 201080019707.7, which claims benefit of PCT/US2010/029957 filed Apr. 5, 2010, which claims benefit of U.S. Appl. No. 12/417,789, filed Apr. 3, 2009.

Clayden J D et al: "Improved segmentation reproducibility in group tractography using a quantitative tract similarity measure" Neuroimage, Academic Press, Orlando, FL, US LNKD-DOI: 10.1016/J.Neuroimage. 2006.07.016, vol. 33, No. 2, Nov. 1, 2006, pp. 482-492.

CLOTALYST™ Automatic Clotting Factor, Would you like to have an autologous thrombin for rapid clotting and haemostasis?, brochure, Biomet Biologics, Inc., Feb. 2007 (12 pages).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May 1976).

Connolly, "Injectable Bone Marrow Preparations to Stimulate Osteogenic Repair," Clinical Orthopaedics and Related Research 313:8-18 (Apr. 1995).

Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.

Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.

De Ugarte, et al., "Comparison of Multi-Lineage Cells from Human Adipose Tissue and Bone Marrow," Cells Tissues Organs 174:101-109 (2003).

De Ugarte, et al., "Differential Expression of Stem Cell Mobilization-Associated Molecules on Multi-Lineage Cells from Adipose Tissue and Bone Marrow," Immunology Letters 89:267-270 (2003).

De Wit, et al. "Experiments on the Preparation of Blood Components with the IBM 2991 Blood Cell Processor" Vox Sang. 29: 352-362 (Feb. 10, 1975).

DelRossi, A. J., A. C. Cernaianu, R. A. Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100:2 (Aug. 1990): 281-6.

DePalma, L., et al., "The preparation of fibrinogen concentrate for use as fibrin glue by four different methods." Transfusion (1993) vol. 33, No. 9; pp. 717-720.

DeUgarte, M.D., Daniel A., et al., "Future of Fat as Raw Material for Tissue Regeneration," (Feb. 2003) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*, ed. 1. Kelman Cohen, Robert F. Diegelmann, and William J. Lindblad. 581-600. 1st ed., vol. Philadelphia: W.B. Saunders Company, 1992.

Ehricke H H et al: "Visualizing MR diffusion tensor fields by dynamic fiber tracking and uncertainty mapping" Computers and Graphics, Elsevvier, GB LNKD-DOI: 10.1016/J.Cag.2006.01.031, vol. 30, No. 2, Apr. 1, 2006, pp. 255-264.

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

Epstein, G. H., R. A. Weisman, S. Zwillenberg, and A. D. Schreiber. "A new autologous fibrinogen-based adhesive for otologic surgery." *Ann Otol Rhinol Laryngol* 95 (May 25-26, 1985) 40-5.

European Communication Pursuant to Article 94(3) EPC mailed May 6, 2013 for PCT/US2010/029957 which claims benefit of U.S. Appl. No. 12/417,789, filed Apr. 3, 2009.

Fibrostik™ Plasma Concentrator, Attention Operating Surgeon, Cell Factor Technologies, Inc., Jul. 2003.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (Aug. 15, 1975): 495-501.

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: The perfect operative sealant?" *Transfusion* 30 (1990): 741-7.

Gimble, Jeffrey M., "Adipose-Derived Stem Cells for Regenerative Medicine," Circulation Research (May 11, 2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (Feb. 29, 2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS® II System, Gravitational Platelet Separation System, "Accelerating the Body's Natural Healing Process," Biomet Biologics (Jul. 15, 2006) 16 pages.

GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, 22, Jan. 2004.

Guilak, Frank, et al., "Adipose-derived adult stem cells for cartilage tissue engineering," Biorheology 41 (2004) pp. 389-399, IOS Press.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.

Harvest SmartPrep PRP-20 Procedure Pack, "Instructions for Use" (date unknown).

Harvest Technologies brochure, SmartPrep2 (2002).

(56) References Cited

OTHER PUBLICATIONS

Hattori, et al., "Osteogenic Potential of Human Adipose Tissue-Derived Stromal Cells as an Alternative Stem Cell Source," Cells Tissues Organs (2004) 178:2-12 Karger.
Haynesworth, S.E. et al, "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).
Hennis, H. L., W. C. Stewart, and E. K. Jeter. "Infectious disease risks of fibrin glue [letter]." *Ophthalmic Surg* 23 (Sep. 1992): 640.
Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).
Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.
Hood, Andrew G., et al., "Perioperative Autologous Sequestration III: A New Physiologic Glue with Wound Healing Properties," (Jan. 1993) vol. 14 pp. 126-129.
International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.
International Preliminary Report on Patentability and Written Opinion mailed Oct. 13, 2011 for PCT/US2010/029957 which claims benefit of U.S. Appl. No. 12/417,789, filed Apr. 3, 2009.
International Preliminary Report on Patentability and Written Opinion mailed Oct. 31, 2013 for PCT/US2012/034104 claiming benefit of U.S. Appl. No. 13/089,591, filed Apr. 19, 2011.
International Preliminary Report on Patentability completed Aug. 13, 2009 for PCT/US2008/004687 claiming benefit of U.S. Appl. No. 60/911,407, filed Apr. 12, 2007.
International Preliminary Report on Patentability mailed Jan. 26, 2012 for PCT/US2010/041942 claiming benefit of U.S. Appl. No. 12/504,413, filed Jul. 16, 2009.
International Search Report and Written Opinion mailed Aug. 9, 2011 for PCT/US2011/031954 claiming benefit of U.S. Appl. No. 12/758,127, filed Apr. 12, 2010.
International Search Report and Written Opinion mailed Jul. 2, 2008 for International Application No. PCT/US2008/004687 which claims priority to U.S. Appl. No. 60/911,407, filed Apr. 12, 2007.
International Search Report and Written Opinion mailed Jul. 3, 2009 for PCT/US2009/035564 claiming benefit of U.S. Appl. No. 61/078,178, filed Jul. 3, 2008.
International Search Report and Written Opinion mailed Jul. 30, 2010 for PCT/US2010/029957 which claims benefit of U.S. Appl. No. 12/417,789, filed Apr. 3, 2009.
International Search Report and Written Opinion mailed Nov. 7, 2011 for PCT/US2011/045290 claiming benefit of U.S. Appl. No. 12/846,944, filed Jul. 30, 2010.
International Search Report and Written Opinion mailed Oct. 8, 2010 for PCT/US2010/041942 claiming benefit of U.S. Appl. No. 12/504,413, filed Jul. 16, 2009.
International Search Report for International Application No. PCT/US/0316506 mailed Oct. 13, 2003 which claims benefit of U.S. Appl. No. 60/383,013, filed May 24, 2002.
International Search Report for International Application No. PCT/US2007/012587 mailed Nov. 6, 2007 which claims benefit of U.S. Appl. No. 11/441,276, filed May 25, 2006.
International Search Report for PCT/US2012/034104 mailed Oct. 29, 2012, claiming benefit of U.S. Appl. No. 13/089,591, filed Apr. 18, 2012.
Invitation to Pay Additional Fees and, Where Applicable, Protest Fee mailed Aug. 6, 2012 for PCT/US2012/034104 claiming benefit of U.S. Appl. No. 13/089,591, filed Apr. 19, 2011.
Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page. (2006).
Jackson, C. M. and Y. Nemerson. "Blood coagulation." Annu Rev Biochem 49 (1980): 765-811.
Japan Office Action mailed Aug. 23, 2013 for Japan Patent Application No. 2010-503066.
Japan Office Action mailed Jan. 22, 2013 for Japan Application No. 2010-503066.
Japanese Office Action mailed May 20, 2014 for Japanese Application No. JP2012-503768.
Jayadev, Suprya. "Trypsinization of Adherent Cells." Aug. 8, 1991. Web. Apr. 14, 2010 http://www.duke.edu/web/ceramide/protocols/0005.html.
Johnstone, et al., "Autologous Mesenchymal Progenitor Cells in Articular Cartilage Repair", Clinical Orthopaedics and Related Research 367S:S156-S162 (Oct. 1999).
Jones D K et al: "Confidence mapping in diffusion ensor magnetic resonance imaging tractography using a bootstrap approach" Magnetic Resonance in Medicine Wiley USA, vol. 53 , No. 5, May 2005, pp. 1143-1149.
Jorgensen, et al., "Stem Cells for Repair of Cartilage and Bone: The Next Challenge in Osteoarthritis and Rheumatoid Arthritis," Annals of Rheumatic Diseases, Aug. 2000.
Journal of Oral Maxillofacial Surgery, vol. 43, pp. 605-611, Helene Matras, M.D., "Fibrin Seal: The State of the Art" (1985).
Karpatkin, S., "Heterogeneity of Human Platelets. VI., Correlation of Platelet Function with Platelet Volume", Blood, vol. 51, No. 2 (Feb. 1978).
Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (1992): 72-3.
Kjaergard, H. K., Fogh Us Weis, and J. J. Thiis. "Preparation of autologous fibrin glue from pericardial blood." *Ann Thorac Sur* 55 (1993): 543-4.
Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.
Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.
Kumar, Vijay et al., "Autologous Thrombin: Intraoperative Production From Whole Blood." Journal of American Society of Extra-Corporeal Technology. JECT: Apr. 2008; 40:94-98.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lasher, Lisa, M.D., "My Experience with PRP," PowerPoint presentation, http://www.cellfactortech.com/global_products.cfm, printed Sep. 16, 2005.
Lendeckel, Stefan, et al., "Autologous stem cells (adipose) and fibrin glue used to treat widespread traumatic calvarial defect's: case report," Journal of Cranio-Maxillofacial Surgery (2004) European Association for Cranio-Maxillofacial Surgery.
Lerner, R. and N. S. Binur. "Current status of surgical adhesives." *J Surg Res* 48 (Feb. 1990): 165-81.
Longas, Maria O., "An Improved Method for the Purification of Human Fibrinogen." J. Biochem (1980) vol. 11, pp. 559-564.
Lori N F et al: "Diffusion tensor fiber tracking of human brain connectivity: acquisition methods, reliability analysis and biological results" NMR in Biomedicine Wiley UK, vol. 15, No. 7-8, Nov. 2002, pp. 493-515.
Lu, et al., "Bone Marrow Mesenchymal Stem Cells: Progress in Bone/Cartilage Defect Repair," 19(1), Jan. 2002.

(56) References Cited

OTHER PUBLICATIONS

Marrowstim Concentration System, Biomet Biologics, Inc., 20 pages (REV Feb. 15, 2008).
Marx, Gerard, et al., "Heat Denaturation of Fibrinogen to Develop a Biomedical Matrix." Journal of Biomedical Materials Research Part B: Applied Biomaterials (Apr. 2007) pp. 49-57.
Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.
Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.
Minivalve international: duckbill valves—du 054.001 sd, <http://www.minivalve.com/htm/DV054.htm>, Accessed Jun. 30, 2014, 1 page.
Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).
Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).
Minntech® Filtration Technologies Group, "Renaflo® II Hemofilter," Minntech Corporation (2004); http://www.minntech.com/ftg/products/renaflo/index.html, printed Jul. 15, 2004 (2 pages).
Molnar, Amy, "Stem Cells from Muscles Can Repair Cartilage, Study Finds Genetically Engineered Muscle-Derived Stem Cells Improved Cartilage Repair in Rats", American College of Rheumatology, (2005).
Momentive Silopren*LSR 2050, Jun. 30, 2014, 3 pages.
Moretz, W., Jr., J Shea Jr., J. R. Emmett, and J Shea. "A simple autologous fibrinogen glue for otologic surgery." *Otolaryngol Head Neck Surg* 95 (Jul. 1986): 122-4.
Nakagami, Hironori, et al., "Novel Autologous Cell Therapy in Ischemic Limb Disease Through Growth Factor Secretion by Cultured Adipose Tissue-Derived Stromal Cells," Angiogenesis by Adipose Tissue-Derived Cells, (Dec. 2005) pp. 2542-2547, American Heart Association, Inc.
Nathan, Suresh et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.
Nilsson, et al., "Bone Repair Induced by Bone Morphogenetic Protein in Ulnar Defects in Dogs," The Journal of Bone and Joint Surgery, vol. 68 B., No. 4, Aug. 1986.
Notice of Allowance mailed Mar. 24, 2011 for U.S. Appl. No. 12/101,586.
Notice of Allowance mailed May 27, 2010 for U.S. Appl. No. 12/101,594, filed Apr. 11, 2008.
Notice of Allowance mailed Oct. 18, 2011 for U.S. Appl. No. 12/897,401.
Office Action (Final) mailed Mar. 18, 2010 for U.S. Appl. No. 12/101,594, filed Apr. 11, 2008.
Office Action mailed Feb. 3, 2011 for U.S. Appl. No. 12/101,586, filed Apr. 14, 2008.
Office Action mailed Nov. 16, 2010 for U.S. Appl. No. 12/897,401 claiming benefit of U.S. Appl. No. 12/101,594, filed Apr. 11, 2008.
Office Action mailed Oct. 16, 2009 for U.S. Appl. No. 12/101,594, filed Apr. 11, 2008.
Office Action mailed Sep. 20, 2010 for U.S. Appl. No. 12/101,586, filed Apr. 14, 2008.
Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

Parchment et al., Roles for in vitro myelotoxicity tests in preclincial drug development and clinical trial planning, Toxicology Pathology, Society of Toxicological Pathologists, vol. 21, No. 2, 1993, pp. 241-250.
Parchment et al., Roles for in vitro myelotoxicity tests in preclinical drug development and clinical trial planning, Toxicology Pathology, Society of Toxicological Pathologists, vol. 21, No. 2, 1993, pp. 241-250.
Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.
Planat-Bénard, V., et al., "Spontaneous Cardiomyocyte Differentiation From Adipose Tissue Stroma Cells," Adipose-Derived Cell Cardiomyocyte (Feb. 6, 2004) pp. 223-229 American Heart Association, Inc.
Ponticiello, Michael S., "A Rapid Technique for the Isolation and Concentration of Stem Cells from Human Bone Marrow", Cell Factor Technologies, Inc. (2006) 2 pages.
Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.
Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (Apr. 15, 2007) pp. 1423-1424.
Sanal, M. "Does fibrin glue cause foreign body reactions? [letter]." *Eur J Pediatr Surg* 3 (1992): 1990 (1 page).
Sanal, M., H. Dogruyol, A. Gurpinar, and O. Yerci. "Does fibrin glue cause foreign body reactions?" *Eu r J Pediatr Surg* 2 (1992): 285-6.
Schmidt, K.G., et al., "Labelling of Human and Rabbit Platelets with Indium-Oxine Complex", 23:97-106 (1979).
Schmidt, K.G., et al., "Preparation of Platelet Suspensions from Whole Blood in Buffer", Scand. J. Hoemato, 23:88-96 (1979).
Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (Apr. 10, 2007) pp. 818-827 AlphaMed Press.
Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.
Sierra, D. H. "Fibrin sealant adhesive systems: a review of their chemistry, material properties and clinical applications." *J Biomater Appl* 7 (Apr. 1993): 309-52.
Sigma-Aldrich® Alkaline Phosphatase (Procedure No. 85), drug fact sheet, (2003) pp. 1-2, Sigma-Aldrich, Inc.
Silver, Frederick H., et al., "Review Preparation and use of fibrin glue in surgery." Biomaterials 16 (1995) pp. 891-903.
Solem, Jan Otto, et al., "Hemoconcentration by Ultrafiltration During Open-Heart Surgery," Scand J Thor Cardiovasc Surg 22:271-274, 1988.
Sutton, Robin G., et al. "Comparison of Three Blood-Processing Techniques During and After Cardiopulmonary Bypass." Ann Thorac Surg (1993) vol. 56; pp. 941-943.
Swift, Mathew J., et al., "Characterization of Growth Factors in Platelet Rich Plasma," 1-Cell Factor Technologies, http://www.cellfactortech.com/global_products.cfm, printed Sep. 16, 2005.
Symphony II Platelet Concentrate System/PCS brochure; "Increasing bone graft bioactivity through reproducible concentrations of natural growth factors," DePuy (Jan. 2003).
Takahashi, Kazutoshi et al., "Induction of Pluripotent Stem Cells from Adult Human Fibroblasts by Defined Factors," Cell, (Nov. 30, 2007) pp. 1-12, Elsevier Inc.

(56) References Cited

OTHER PUBLICATIONS

The American Journal of Surgery, vol. 168, pp. 120-122, Aug. 1994, Roy L. Tawes, Jr., M.D., et al., "Autologous Fibrin Glue: The Last Step in Operative Hemostatis".
The American Surgeon, vol. 55, pp. 166-168, Mar. 1989, William D. Spotnitz, M.D., et al., "Successful Use of Fibrin Glue During 2 Years of Surgery at a University Medical Center".
The Sports Medicine Center, "Knee Cartilage Implantation", Carticel™, "Autologous Cultured Chondrocyte Implantation", http://www.orthoassociates.com/carticel.htm (printed Apr. 6, 2006).
The Stone Clinic, "Platelet Rich Plasma (PRP)", web site printed May 2006.
Vernay Product Information Sheet, Umbrella Check Valve, Part No. V251010200, Jul. 2013, 2 pages.
Weis-Fogh, U. S. "Fibrinogen prepared from small blood samples for autologous use in a tissue adhesive system." Eur Surg Res 20 (1988): 381-9.
Weisman, MD., Robert A., "Biochemical Characterization of Autologous Fibrinogen Adhesive," Laryngoscope 97: Oct. 1987; pp. 1186-1190.
Wiseman, David M., David T. Rovee, and Oscar M. Alverez. "Wound Dressings: Design and Use." in *Wound Healing: Biochemical & Clinical Aspects*, ed. I. Kelman Cohen, Robert F. Diegelmann, and William J. Lindblad. 562-580. 1st ed., vol. Philadelphia: W. B. Saunders Company, 1992.
Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).
Written Opinion of the International Preliminary Examining Authority mailed Mar. 17, 2009 for International Application No. PCT/US2008/004687 which claims priority to U.S. Appl. No. 60/911,407, filed Apr. 12, 2007.
Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.
Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.
Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert Inc.
"European Application Serial No. 09717764.6, Communication Pursuant to Article 94(3) EPC mailed Jan. 18, 2017", 4 pgs.
"European Application Serial No. 09717764.6, Communication Pursuant to Article 94(3) EPC mailed Feb. 17, 2011", 3 pgs.
"European Application Serial No. 09717764.6, Communication Pursuant to Article 94(3) EPC mailed Mar. 9, 2016", 4 pgs.
"European Application Serial No. 09717764.6, Communication Pursuant to Article 94(3) EPC mailed Apr. 25, 2012", 4 pgs.
"European Application Serial No. 09717764.6, Invitation pursuant to Article 94(3) and Rule 71(1) EPC mailed Nov. 25, 2013", 2 pgs.
"European Application Serial No. 09717764.6, Response filed Mar. 28, 2014 to Invitation pursuant to Article 94(3) and Rule 71(1) EPC mailed Nov. 25, 2013", 34 pgs.
"European Application Serial No. 09717764.6, Response filed Jun. 24, 2011 to Communication Pursuant to Article 94(3) EPC mailed Feb. 17, 2011", 14 pgs.
"European Application Serial No. 09717764.6, Response filed Sep. 5, 2012 to Communication Pursuant to Article 94(3) EPC mailed Apr. 25, 2012", 14 pgs.
"European Application Serial No. 09717764.6, Response filed Jul. 19, 2016 to Communication Pursuant to Article 94(3) EPC mailed Mar. 9, 2016", 18 pgs.

\* cited by examiner

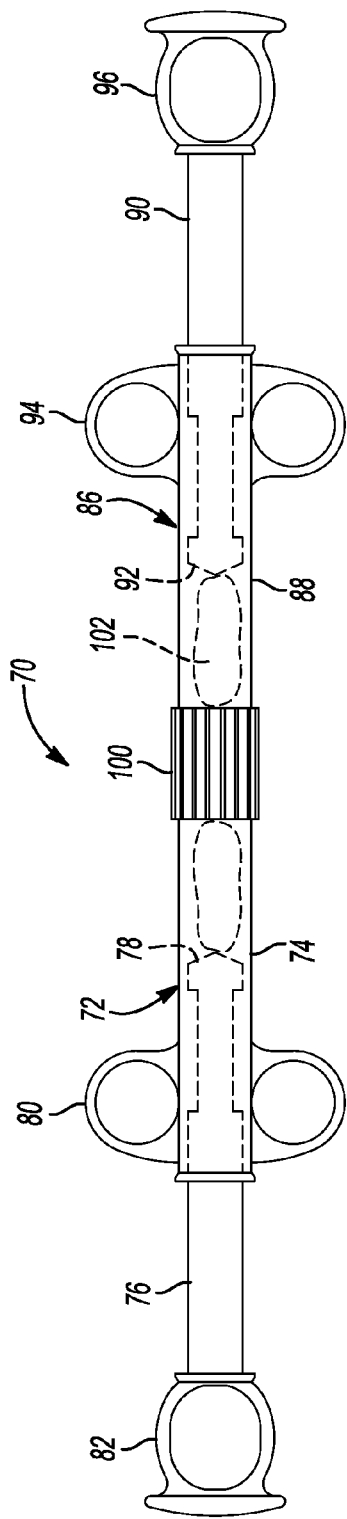
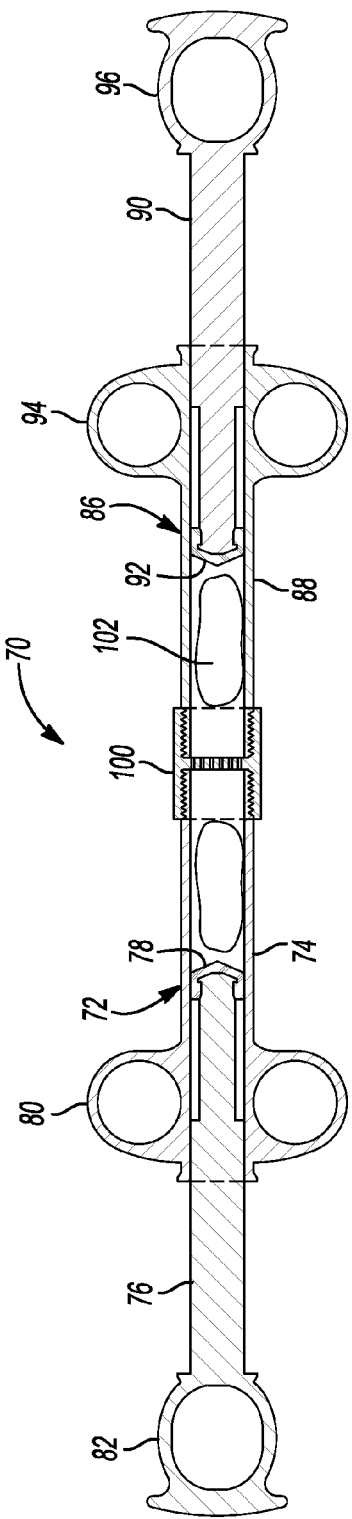

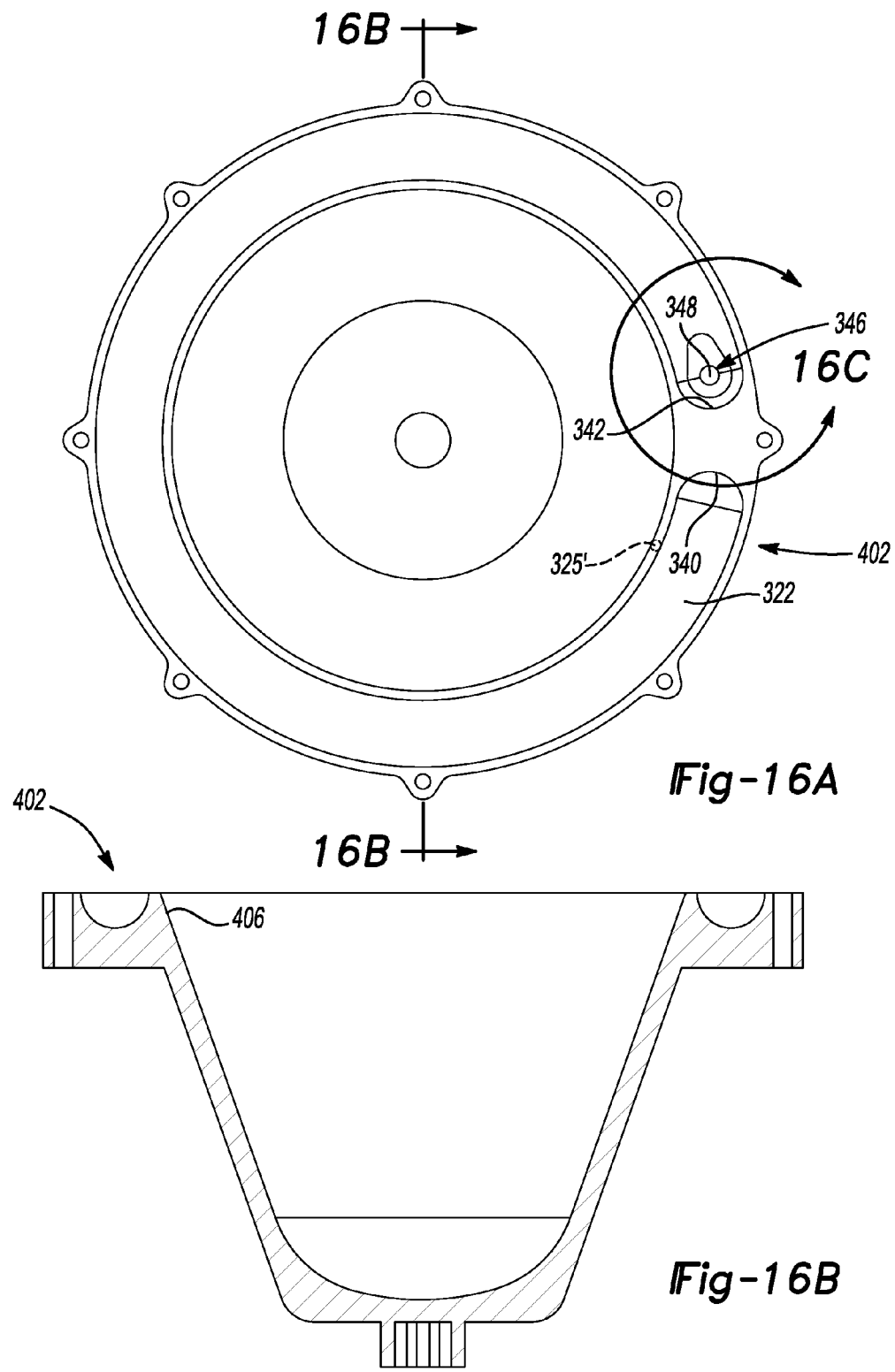

SYSTEM AND PROCESS FOR SEPARATING A MATERIAL

CROSS-REFERENCE TO RELATED APPLICATIONS

This application is a divisional of U.S. patent application Ser. No. 13/721,978 filed on Dec. 20, 2012, now U.S. Pat. No. 8,801,586 issued Aug. 12, 2014, which is a divisional of U.S. patent application Ser. No. 12/395,085 filed on Feb. 27, 2009, now U.S. Pat. No. 8,337,711 issued Dec. 25, 2012, which claims the benefit of: (1.) U.S. Provisional Application No. 61/032,619 filed on Feb. 29, 2008, and (2.) U.S. Provisional Application No. 61/078,178 filed on Jul. 3, 2008. The disclosures of the above applications are incorporated herein by reference.

FIELD

The present disclosure relates generally to separation of a selected component from a multi-component biological material.

BACKGROUND

The statements in this section merely provide background information related to the present disclosure and may not constitute prior art.

Various cellular (or biological) materials can be used to assist a person in a healing or recovery process. Pluripotent cells, multi-potent cells, stem cells, or fully differentiated cells can be applied to a patient for providing therapy to the patient. For example, stem cells can be applied to a patient to assist in healing an affected area through differentiation of the stem cells. In addition, stem cells can be applied to an area of the patient that may be damaged due to injury, chemotherapy, or radiation therapy to assist in regeneration of the affected cells.

Stem cells can be acquired from various sources. Selected sources can include autologous sources, where the patient is a donor or self donor. The autologous source of the stem cells can include various tissues, such as adipose tissue. Adipose tissue can be used as a source of cells, such as stem cells or vascular endothelial cells that can be separated, concentrated, or purified from the fat cells.

SUMMARY

A selected cell population from a selected tissue sample, such as adipose tissue, can be separated, enriched, and/or purified. The selected cell population can include pluripotent, multipotent, or stem cells or other cells having therapeutic value for use in a therapy. The population can be collected via aspiration or excision of a tissue sample and further processed for separation and purification of the selected cells from the tissue sample. Therapeutic non-cellular material (for example extracellular matrix) can also be separated and purified. The tissue sample can include adipose tissue, mucosa, muscle, blood, or other appropriate tissue sources.

The tissue sample can be acquired from a patient and separated in an efficient and time effective manner for application to the same patient (i.e. autologous). Use of autologous cells can reduce possible rejection and reduce contamination issues. Further, autologous cells can provide a genetic match to the patient.

A process for acquiring a tissue sample, according to various embodiments, can generally include aspirating or excising adipose tissue from a patient. The aspirated or excised adipose tissue can then be disrupted, macerated, and/or pulverized. The disrupted tissue can then be separated using a separation system as discussed herein. In the separation system, the disrupted tissue can be suspended in a selected biologically acceptable solution that can aid in separation or enrichment of a selected fraction of cells.

A system for separating the selected fraction of cells from the tissue sample can include a container that is operable to rotate around a central axis so that the tissue sample is moved towards or pressed against an outer wall (such as centrifugal forces) and separated based upon size and/or density. Areas of different size or density can be formed between the central axis and the outer wall. The separation device can also have a separate concentric ring or collection area that can collect a selected fraction of the material, such as a selected cell fraction, and a closure valve for the collection area. Disruption devices, according to various embodiments, including those discussed herein, can be used to disrupt the tissue sample prior to the separation of the selected fraction in a separation system.

Although the present disclosure may refer to aspirate or lipoaspirate, it will be understood that any appropriate tissue sample may be used, unless specifically indicated otherwise. For example, muscle or mucosa tissue can be excised, disrupted, and separated as discussed herein. In addition, adipose tissue may also be excised rather than only aspirated.

In addition, a selected fraction, such as a selected cell fraction, can include stem cells. It will be understood, however, that stem cells can be used herein, unless otherwise specified, to indicate cells that are undifferentiated or incompletely differentiated and able to differentiate into more than one cell type. For example, a stem cell may be able to differentiate, depending upon various factors, into one or more distinct cells. Certain populations of cells, however, may only differentiate into one, two, or any discrete number of cell types. Also, a selected fraction can include cells that are unlimited or limited in their differentiation possibilities. Undifferentiated cells can also include pluripotent or multipotent cells. These cells can differentiate into an appropriate number of cell types.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3A is a plan view of a tissue disruptor, according to various embodiments;

FIG. 3B is a cross-sectional view of the disruptor of the FIG. 3A;

FIGS. 16A-16D are various detailed views of the tissue isolator of FIG. 15;

DETAILED DESCRIPTION

The following description is merely exemplary in nature and is not intended to limit the present disclosure, application, or uses.

Figure 1:
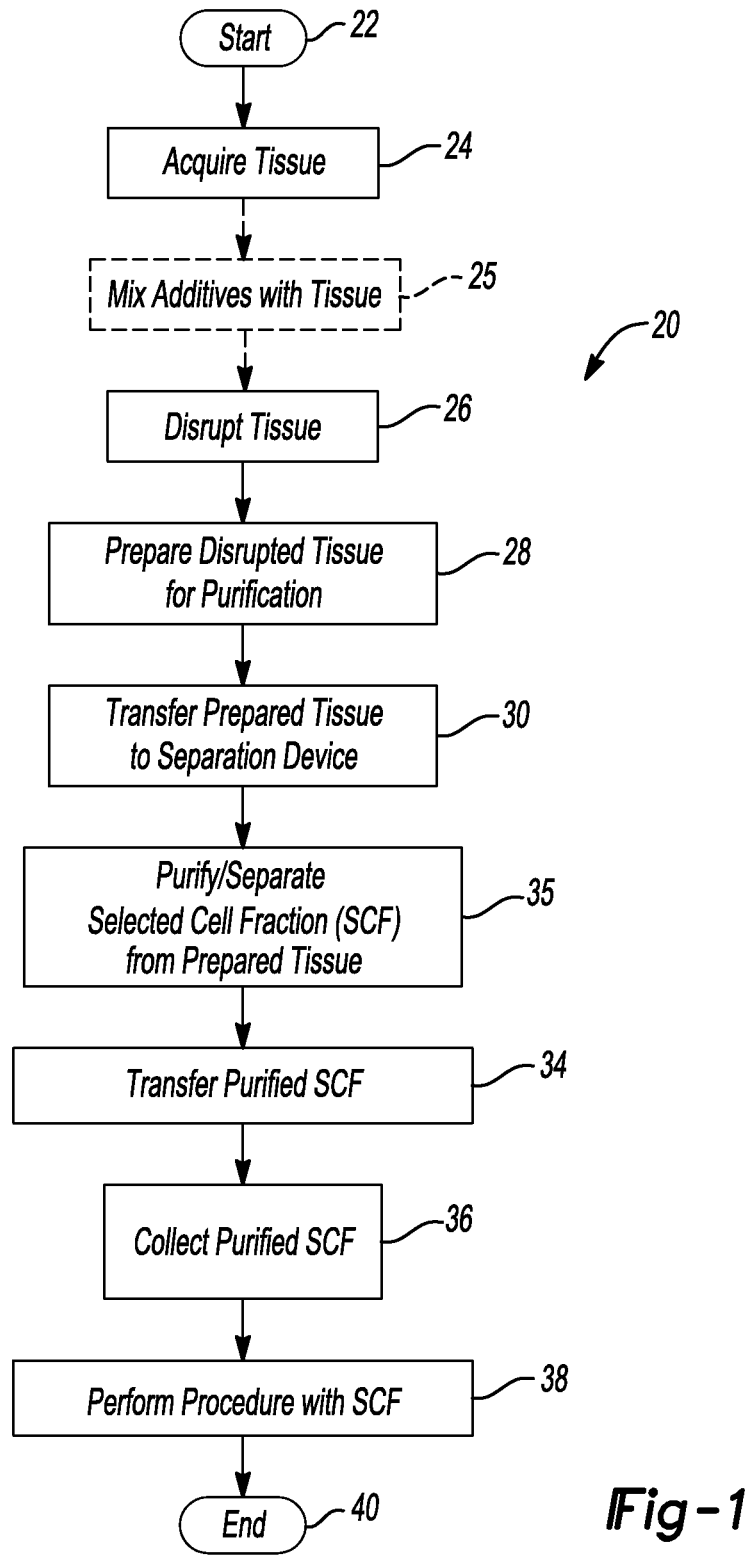
FIG. 1 is a flowchart illustrating a general process for tissue separation.

With reference to FIG. 1, a flow chart 20 illustrates a general process of acquiring a selected fraction of cells from a tissue sample. A selected fraction can include a cell population, such as stem cells or other undifferentiated cell populations, as discussed above. According to various embodiments, the process starts at Start block 22. Any appropriate tissue sample, (e.g. adipose tissue) can be acquired in block 24. If the selected tissue is adipose tissue, it can be acquired in various techniques, such as during liposuction, aspirating adipose tissue from a selected source, or other appropriate techniques. For example, during a prosthesis implantation, adipose tissue can be excised or removed from the patient near or at the incision for the prosthesis implantation. Therefore, aspiration of tissue is merely an exemplary process for withdrawing or removing tissue from a patient.

The tissue sample can be mixed or suspended with an appropriate additive in optional block 25. Additives can include materials to adjust pH or for chelating, such as citrate. A pH can be selected to be about 4 to about 9, and can be selected to be about 4 to about 6. Other additives can include lytic activity materials (for example, RBC lysis buffer), ion channel blockers, anti-apoptosis agents, protease inhibitors, density modifiers, chaotropic agents, osmolarity altering agents (to differentially alter density and/or fragility of subpopulations of cells), and/or detergents. These additives can alter pH, chelate various ions, etc. The additives, however, generally are enzyme free. Thus, enzymes are generally not, and need not be added to the tissue sample. In addition, any additive is optional and may not be added until the tissue sample is prepared for separation after processing. The solution or the tissue can be maintained at about 35 to 45 degrees centigrade (C).

The tissue can be disrupted in block 26. The disruption of the tissue can occur according to any appropriate technique or with any appropriate device, including those described further herein and may include adding additives, as described above. Nevertheless, the disruption of the tissue can generally be performed to obtain a selected cluster or particle size of the tissue. For example, it may be selected to obtain clusters of tissue (including cells and intercellular matrix) that are about 0.1 mm to about 5 mm, in size including about 0.5 mm to about 2 mm, and also including about 1 mm in average size. It will be understood that clusters of tissue may not be perfect spheres or other geometric shapes and therefore the average size can include a diameter dimension, a size defined by random measurement, a sieve measurement, or any other appropriate measurement, such as microscopy, coulter counting, laser light scattering and other techniques well known to those skilled in the art. In addition, an adipose tissue sample can be disrupted to about 0.5 mm to about 2 mm, including about 1 mm in average cluster size.

A selected cell fraction or population can be prepared for separation from the tissue sample in block 28. The tissue can be suspended in a selected suspension material or otherwise prepared for separation. For example, a chelating agent, such as citrate, can be mixed with the disrupted tissue. The citrate, or other chelating agent, can weaken the bonds between cells, cells and an extracellular matrix, and between cells, the extracellular matrix, and other components in the extracellular matrix. Thus, citrate or other appropriate materials can assist in separation of a selected cell fraction. Further, citrate or other similar materials, such as chelating compounds, can assist or enhance separation without the addition of enzymes.

In addition, the solution can be maintained or provided at a selected pH for purification or separation. It will be understood, the addition of an acid or a base can be used to acquire a selected pH. Also, the addition of various materials, such as the citrate, can alter or be used to provide a selected pH of the material for separation.

The tissue can be suspended in a solution to assist with separation. For example, the tissue can be placed in an intermediate density solution (e.g. Ficoll® copolymers sold by GE HEALTHCARE BIO-SCIENCES AB of SWEDEN) where adipose tissues can rise. The combination of the intermediate density solution and tissue can also be centrifuged, as discussed further herein. Centrifugation with an additional solution, in addition to the tissue, is not necessary.

Other additives can also be added for various purposes as discussed above. Materials, however, need not be added. This is true regardless of whether a material has already been added.

Once the tissue has been prepared for purification, the tissue can be placed into a separation or purification device in block 30. Placing the tissue sample in the device in block 30 can include transferring the tissue cells and any additive materials previously added. It will be understood that additives need not be provided. The transfer of the prepared tissue to the separation device in block 30 can be performed in any appropriate manner. For example, the material can be transferred in a syringe (e.g. sterile syringe), a transfer container, a sterile syringe, or any appropriate technique. Various transport systems can include those disclosed in U.S. patent application Ser. No. 11/222,303, filed Sep. 8, 2005, now U.S. Pat. No. 7,766,900, issued Aug. 3, 2010, commonly assigned, and incorporated herein by reference.

The selected cell fraction can then be separated in block 32. The separation of the selected cell fraction can occur according to various embodiments, including those discussed further herein. For example, the GPS™ separation system, sold by Biomet Inc. of Warsaw, Ind., USA can be used to separate the selected cell fraction from tissue. Exemplary buoy separation systems are disclosed in U.S. patent application Ser. No. 10/932,882, filed on Sep. 2, 2004, now U.S. Pat. No. 7,374,678, issued May 20, 2008, incorporated herein by reference. The buoy or separation device can be designed with an appropriate density or specific gravity for stem cell separation from adipose tissue, or other appropriate separations. Further, separation devices can include those discussed further herein.

The purified selected cell fraction can be transferred in block 34, according to various embodiments, automatically or manually to a selected or isolation area. For example, a separation device can be used that includes a separation area and a collection area where the purified selected cell fraction is collected substantially automatically during a separation process. Therefore, the transfer of the purified cells in block 34 is optional and other collection techniques can be used. Regardless, a collection of the selected cell fraction occurs in block 36. The selected cell fraction that is purified can be collected in any appropriate manner, as discussed further herein. In block 38, an optional procedure can be performed with the selected cell fraction. Accordingly, the procedure may end at END block 40 after collecting the purified selected cell fraction with or without performing a procedure with the collected cells. Nevertheless, a selected procedure can be performed, such as applying the selected cell fraction to a patient or using the selected cell fraction in a selected therapeutic procedure. It will be understood, however, that the selected cell fraction can also be used for various other procedures, such as research, seeding a scaffold (i.e., building an ex-vivo structure), cell line creation, and the like.

Figure 2:
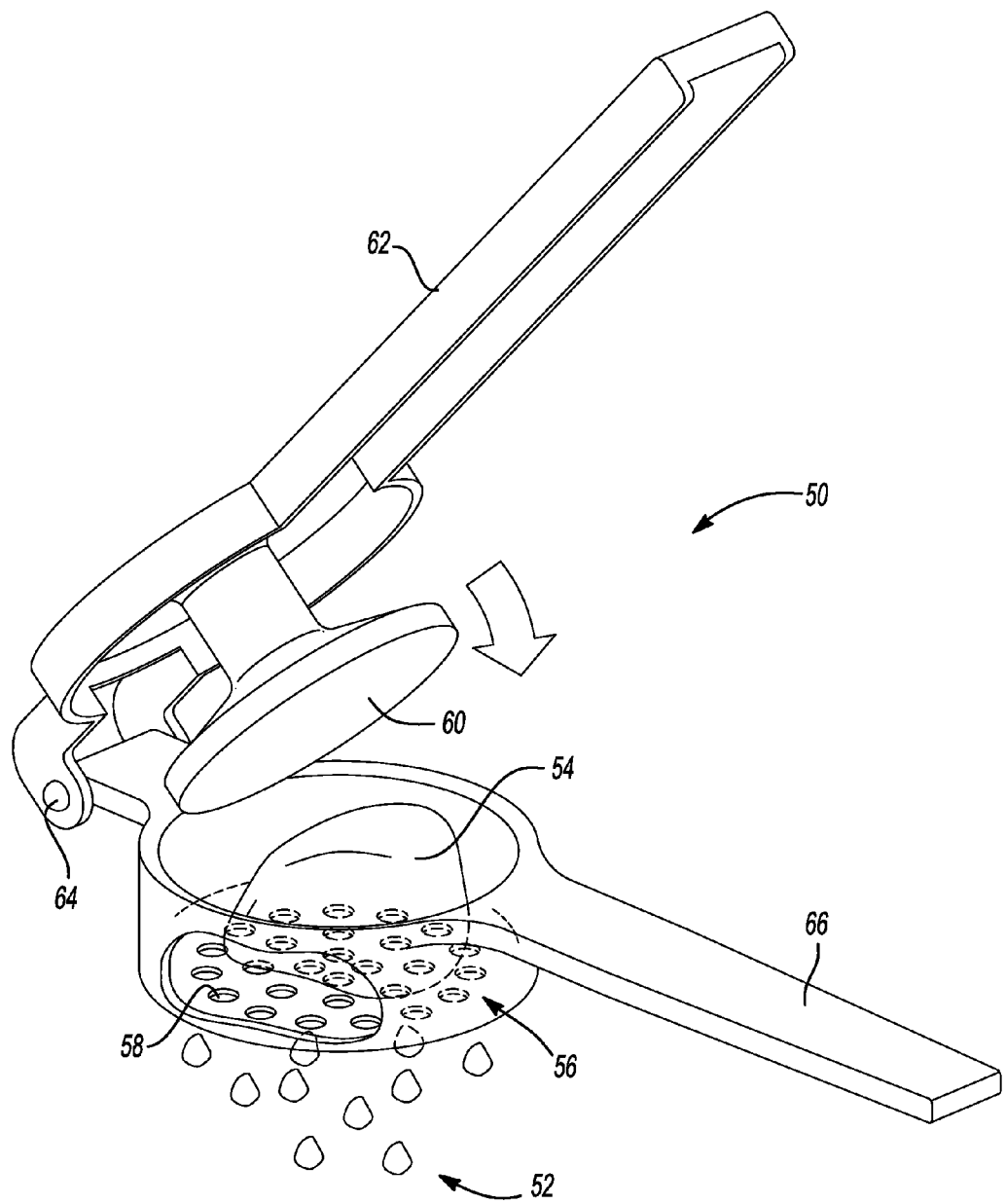
FIG. 2 is a perspective view of a tissue disruptor, according to various embodiments.

With reference to FIG. 2, a disruption device can include a mechanical press 50. The mechanical disruption device 50 can be used to create disrupted tissue 52 from aspirated or collected tissue 54. The mechanical disruption device 50 can include a collection area 56 into which the initially collected tissue 54, collected according to various appropriate procedures, is placed. The collection area 56 can include a frit or screen 58 through which the undisrupted tissue can be forced to create the disrupted tissue 52. The undisrupted tissue 54 can be forced through the frit 58 with a press portion 60 that is adapted or configured to fit within the collection 56 and force the undisrupted tissue 54 through the frit 58. A mechanical force can be applied to a lever arm 62 to which the press portion 60 is connected to force the undisrupted tissue 54 through the frit 58. A fulcrum 64 can interconnect the lever arm 62 of the press portion 60 with a second arm 66 which can define or be connected with the collection area 56. After disruption, the disrupted tissue 52 can be processed according to the method 20, illustrated in FIG. 1, and further herein. It will be understood that the tissue can include an adipose tissue sample.

With reference to FIGS. 3A-4B, a dual syringe or reciprocating syringe and disruption frit assembly 70 is illustrated. The dual syringe system can include a first syringe assembly 72 including a cylinder 74 defining a wall and an interior and a piston rod and/or plunger 76. The piston rod 76 with the syringe assembly 72 can terminate in a plunger or stopper member 78. To assist in reciprocation or movement of the plunger 78, the syringe assembly 72 can include finger holds or holding members 80 connected with the cylinder 74 and a second finger grasping portion 82 interconnected with the rod 76.

A second syringe assembly 86 can be provided also including a cylinder 88 and a rod portion 90 that terminates in a plunger 92. Similar grasping portions 94, 96 can be interconnected with a cylinder 88 and rod 90. The two syringes can be interconnected with a frit member 100. The two syringe assemblies 72 and 86 can be used to move a sample 102 through the frit assembly 100 between the two cylinder bodies 74, 88. The movement through the frit assembly 100 can disrupt the adipose tissue in a defined manner.

Figure 4A:
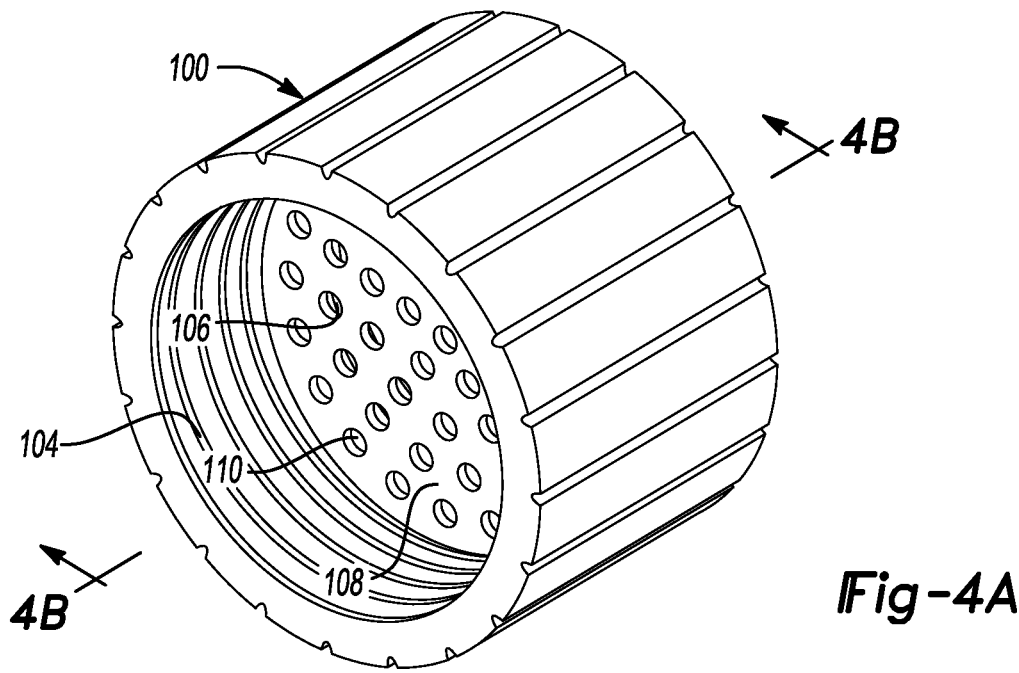
FIG. 4A is a frit assembly, according to various embodiments.
Figure 4B:
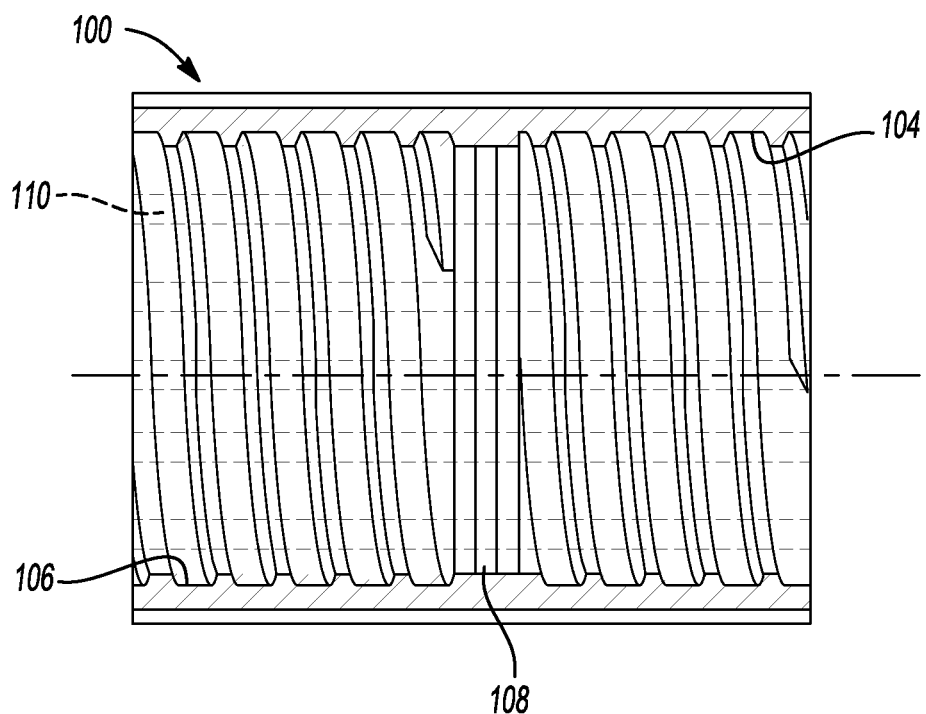
FIG. 4B is a plan and transparent view of the assembly of FIG. 4A.

With reference to FIGS. 4A, 4B, the frit assembly 100 can include two threaded portions; a first threaded portion 104 and a second threaded portion 106. The two threaded portions 104, 106 of the frit assembly 100 allow the first syringe assembly 72 and the second syringe assembly 86 to engage a threaded coupling the frit assembly 100. It will be understood that other coupling mechanisms, such as a friction or interference fit, can be provided to couple the syringes to the frit assembly 100. Thus, the first and second syringe assemblies 72, 86 can be selectively connected with the frit assembly 100. This can also be used to allow for loading or unloading of the tissue sample. For example, one or both of the syringe assemblies 72, 86 can be disconnected from the frit assembly 100 and the tissue sample can be loaded into one or both of the syringe assemblies. As discussed further herein, the syringe assemblies 72, 86 can then be used to reciprocate the tissue sample through the frit member 108 to disrupt the tissue sample, as discussed further herein.

A frit member or body 108 can include one or more throughbores or passages 110 that allow material to pass, such as tissue, as the two syringe assemblies 72, 86 are used to reciprocate the sample through the frit body 108. The sample is forced through the holes 110 with the syringe assemblies 72, 86. The reciprocation mechanically disrupts the tissue and an appropriate number of reciprocations can occur to achieve a selected disruption of the tissue sample. Furthermore, the holes 110 in the frit body 108 can be provided in any appropriate dimension, such as a diameter, to achieve a selected disruption of the fat. Therefore, a dual or reciprocating syringe assembly 70 can also be used to disrupt the tissue sample in block 26 of the method 20. Again, the tissue sample can include an adipose tissue sample from an appropriate source.

The holes 110 defined in the frit body 108 can include any appropriate dimension. For example, the frit holes can include a dimension of about 0.02 inches to about 1 inch, including about 0.04 inches to about 0.5 inches, such as about 0.25 inches. The dimension of the holes 110 can be any appropriate dimension and may vary depending upon the cell type to be enriched or concentrated from the tissue sample. Also, the hole size can be provided according to the source of the tissue sample to be disrupted. For example, a lipoaspirate originated sample may be disrupted with a smaller opening to achieve a selected particle size as opposed to a sample from another source, such as a sample from an abdominoplasty.

Moreover, a kit including a plurality of the frit assemblies 100 can include multiple frit bodies with different holes of different dimensions. Therefore, a user can select an appropriate frit dimension depending upon the source of the adipose tissue. Moreover, an adipose tissue that is being disrupted can be moved through a plurality of frit assemblies. The kit can include a plurality of the frit assemblies 100 including hole dimensions that may be progressively smaller so that the adipose sample can be moved through progressively smaller hole dimensions to progressively increase disruption of the fat or adipose tissue sample. For example, as discussed above, a first frit assembly 100 including a first selected hole dimension can be interconnected with both of the syringe assemblies 72, 86. The tissue sample can be disrupted by reciprocating the syringe assemblies 72, 86 and after a selected period of time or cycles of reciprocation, the first frit assembly can be replaced with a second frit assembly having holes 110 of a different dimension. The syringe assemblies 72, 86 can then be reciprocated to disrupt the tissue with the different hole dimension size for a selected period of time or number of cycles. This can be repeated until selected tissue sample particle size or disruption size has been achieved.

According to various embodiments, a single syringe, as opposed to a dual syringe, with an appropriate frit assembly can also be used for disruption. A single syringe can operate similarly to the duel syringe, save that the material can be expressed through the frit to a collection container or area. In addition, the frit assembly, according to various embodiments, can include a single passage or orifice for disruption. Examples of a single orifice frit can include an aspiration needle. Various embodiments can include single plungers, as discussed herein, with various mechanical assist mechanisms. Various frits of differing passage diameters can be provided for appropriate disruption of the sample.

Figure 5:
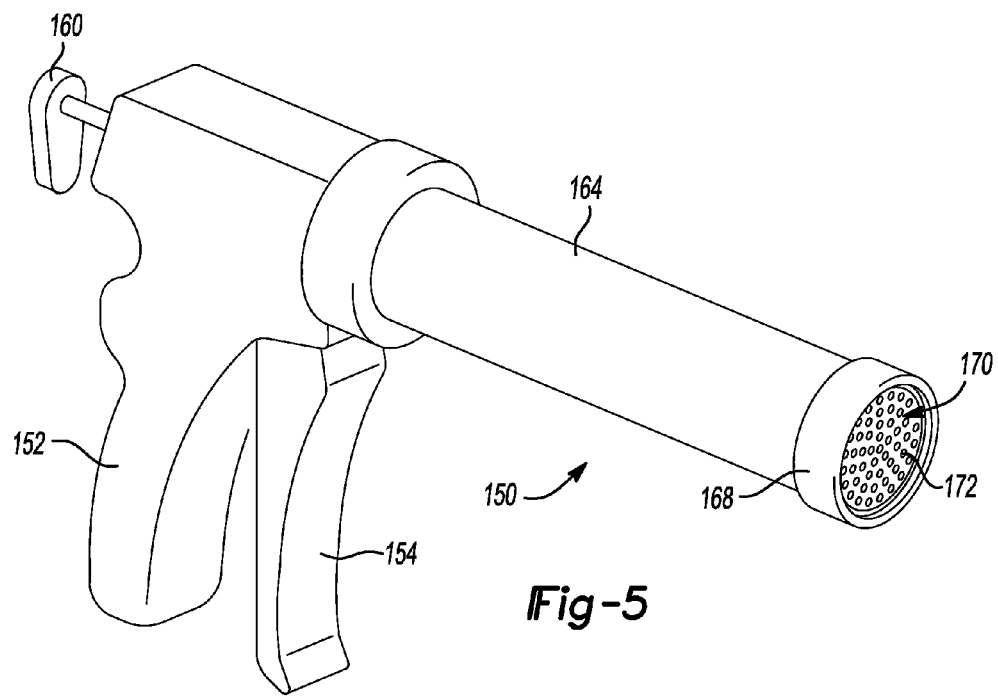
FIG. 5 is a perspective view of a tissue disruptor, according to various embodiments.
Figure 6:
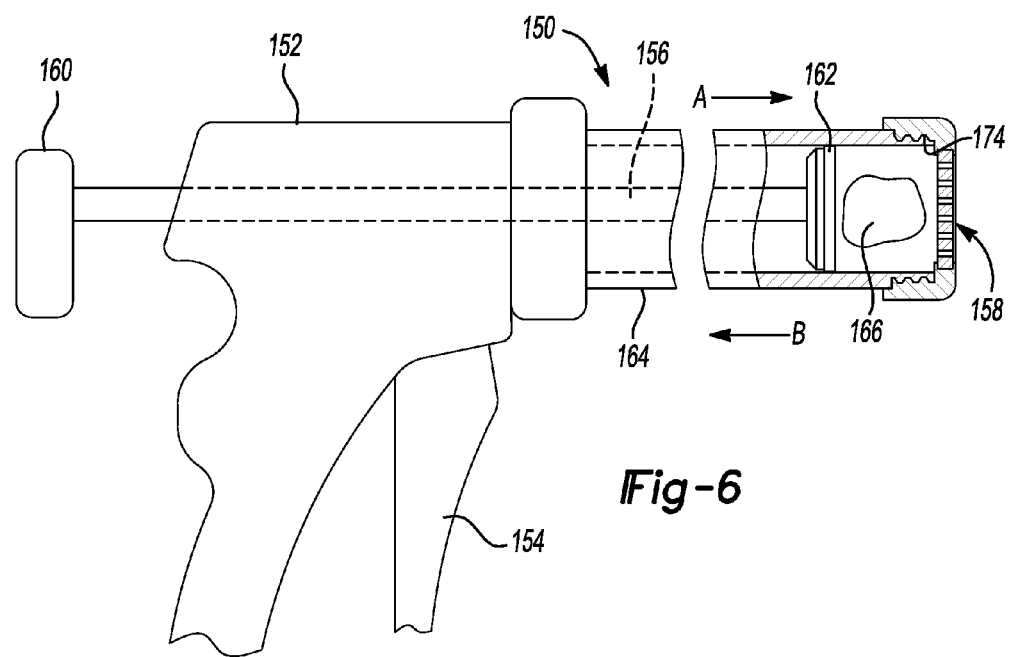
FIG. 6 is a plan view of a tissue disruptor, according to various embodiments.

According to various embodiments, a disruption assembly 150 is illustrated in FIGS. 5 and 6. The disruption assembly 150 can include a single pass, non-reciprocating bone cement gun configuration. Various such bone cement gun assemblies include the Optigun™ assembly sold by Biomet, Inc. of Warsaw, Ind., USA as a part of the Optivac™ Cement Mixing System. Briefly, the bone cement gun assembly 150 can include a main handle portion 152 and a power actuating handle 154. Generally, the power handle 154 can move relative to the main handle 152 to cause a movement of an actuating rod 156. The connection of the handles 152, 154 and the rod 156 can be any appropriate connection. For example, a pawl and ratchet system can be used to advance the rod 156 in a selected direction, such as the direction of arrow A towards an exit end of 158 of the assembly 140. A release mechanism can be depressed or moved to allow withdrawal or movement of the rod 156 in a direction of an arrow B towards the handle assembly 152. Movement of the rod 156 towards the handle assembly can be performed via manual movement or automatic movement, such as pulling on a retraction handle 160.

The rod 156 can terminate in a plunger 162 held within a canister or tube 164. Near the exit end 158 of the tube 164 can be a frit or disruption assembly 168. A sample of tissue 166, such as adipose tissue, can be introduced into the tube 164 for purposes of disruption. The sample of tissue can be introduced into the tube 164 in various manners. For example, the frit assembly 168 can be removed or the entire tube 164 can be removed from the trigger body. In this way, a sample can be introduced into the tube 164 for disruption or extrusion through the frit assembly 168.

The frit assembly 168 can include a frit body 170 that defines one or more passages or holes 172. The passages 172 can include any appropriate dimension, such as those discussed above. As the assembly 150 is actuated, the plunger 162 can move the adipose tissue sample 166 through the holes 172 defined in the frit assembly 168. This can cause a mechanical disruption of the sample 166 as it passes through the frit assembly 168.

As discussed above, the frit assembly 168 can include any appropriate frit or hole dimensions. Also, the holes, according to various embodiments, can be provided in any appropriate shape or configuration. Further, the frit assembly 168 can be removable, such as via a threaded interconnection with threads 174 so that the frit assembly 168 can be applied or removed from the tube 164. This can allow for introduction of the sample into the tube 164 or exchange of the frit assemblies 168. For example, a kit can include a plurality of the frit assemblies 168, each including different dimensions of the throughbores 172. The tissue sample 166 can be pressed through a first frit assembly 168, the first frit assembly can then be removed, the sample replaced in the tube 164, a different frit assembly positioned on the tube 164, and the sample again pressed through the new frit assembly. Therefore, the tissue sample can be progressively and increasingly disrupted as it moves through a plurality of the frit assemblies.

Figure 7:
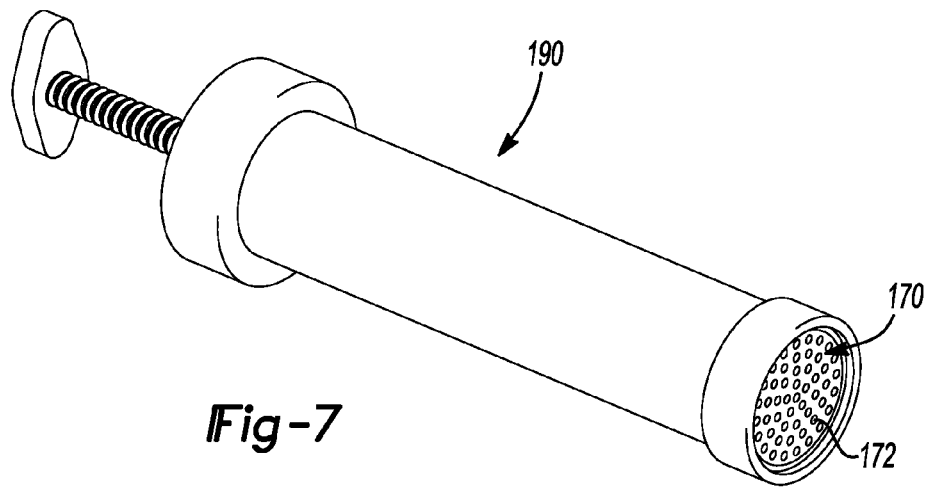
FIG. 7 is a tissue disruptor, according to various embodiments.
Figure 8:
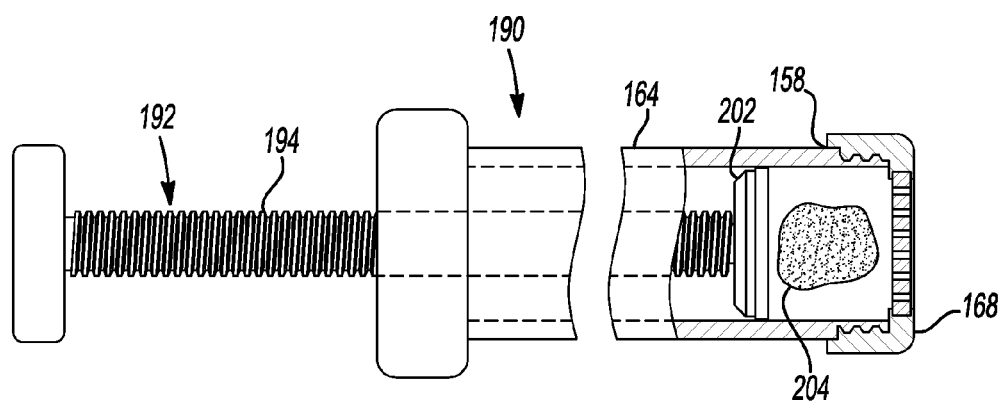
FIG. 8 is a plan view of the tissue disruptor of FIG. 7.
Figure 9:
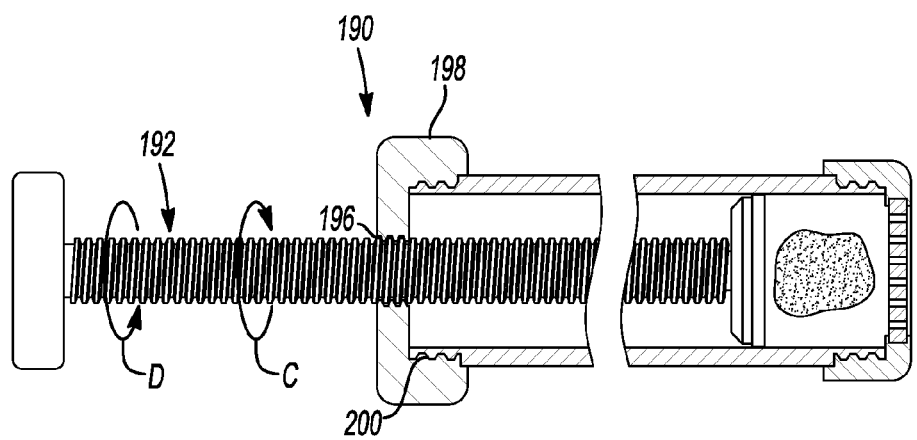
FIG. 9 is a plan transparent view of the tissue disruptor of FIG. 7.

With references to FIGS. 7-9, a disruption assembly 190 is illustrated. The disruption assembly 190 can include portions that are similar to the disruption assembly 150 and similar reference numerals are used to identify these portions and discussed again only briefly. For example, the disruption assembly 190 can include a tube 164 that has a terminal or exit end 158 and a frit assembly 168 positioned near the terminal or exit end 158. The frit assembly 168 can include a frit body 170 that defines one or more throughbores or holes 172. As discussed above, an aspiration needle could be considered one very long hole.

The disruption assembly 190 can include a rod 192 that defines an external thread 194. The external thread can engage an internal thread 196 defined in an end cap or end portion 198 of the disruption assembly 190. The end cap 198 can be removable from the tube 164 via a threaded engagement 200. The rod 192, however, can be rotated in an appropriate direction, such as the direction of arrow C to advance the rod towards the exit end 158 that, in turn, can push a plunger 202 towards the exit end 158. A sample 204, such as an adipose tissue sample, can be pressed through the holes 172 defined by the frit body 170 in the frit assembly 168. The rod 192 can also be rotated in a counter direction, such as generally in the direction of arrow D, to move the plunger 202 towards the end cap 198. This can allow the plunger 202 to be moved back and forth within the tube 164 and can allow for filling of the tube 164, such as with removal of the frit assembly 168. Further, as discussed in relation to the disruption assembly 150, a kit can include a plurality of the frit assemblies 168 each including holes 172 of different sizes. Therefore, the sample 204 can be pushed through a frit assembly including a first hole size and reloaded into the tube 164 and pushed through a second frit assembly including a second hole size.

Regardless of the configuration of the disruption assembly, it can be selected to disrupt a tissue sample to a selected particle or cluster size. For example, the cluster sizes can be selected to be any appropriate dimension, such as those discussed above. Further, as discussed in relation to the various disruption assemblies, one or more passes through one or more frit assemblies may be selected to achieve an appropriate particle size. Therefore, it will be understood that a disruption can include one or more passes through a frit assembly and various procedures, such as quality control procedures, can be used to ensure that an appropriate particle size is achieved. Therefore, the disruption assemblies, according to various embodiments, can be provided alone or in combination with other disruption assemblies to achieve an appropriate particle size, such as those discussed above.

Regardless of the disruption assembly provided, once disruption occurs the disrupted sample can be further separated or purified to acquire a selected component, such as a selected cell population. For example, a pluripotent or stem cell population can be extracted from the tissue sample (e.g. disrupted adipose tissue). Various techniques can be used to separate the pluripotent or stem cells from the disrupted tissue including those discussed further herein.

Figure 10:
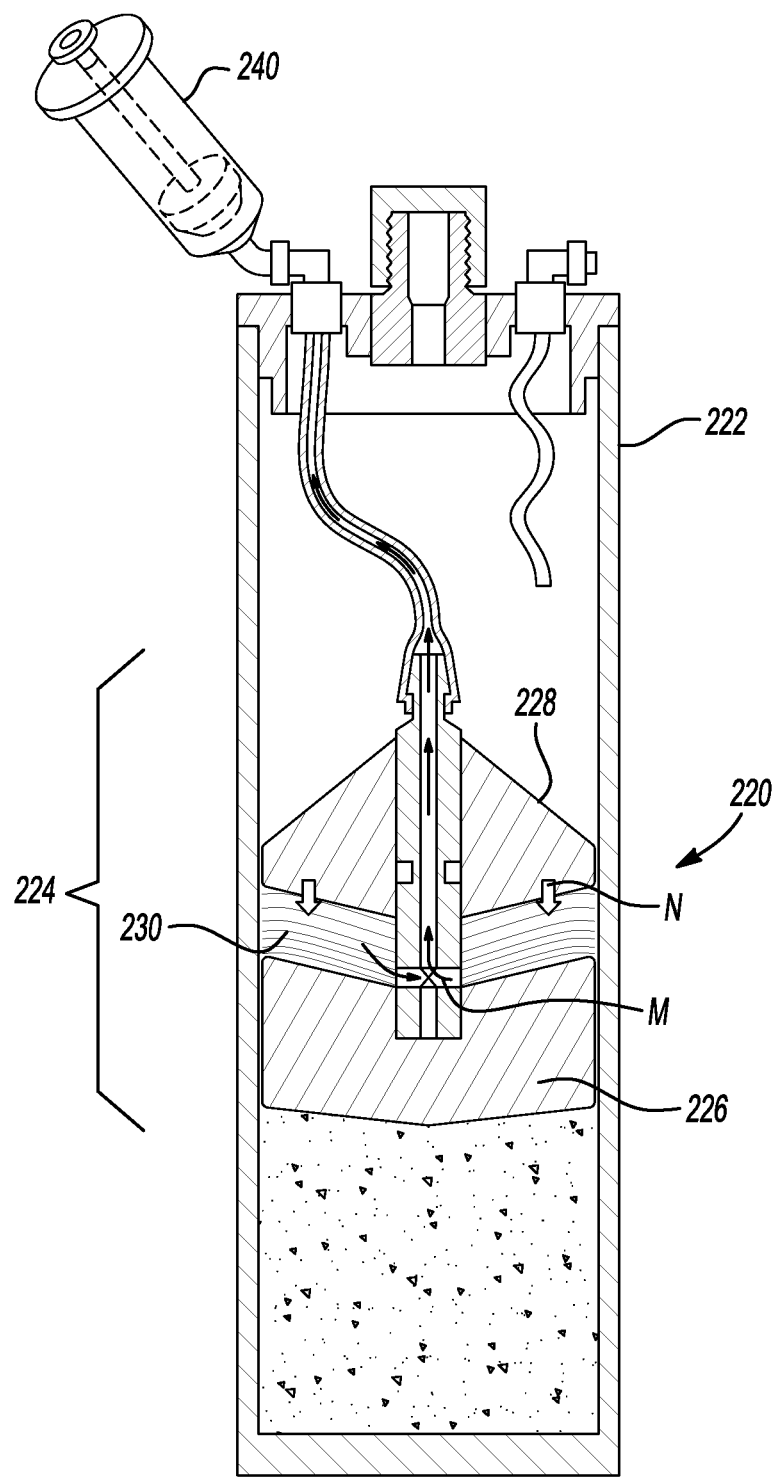
FIG. 10 is a cross-sectional view of a tissue isolator, according to various embodiments.

With reference to FIG. 10, a tube or separation assembly 220 can be used. A separation assembly 220 can include a tube 222 and a separation buoy system 224. The buoy system 224 can include a first buoy member 226 and a second buoy member or isolator portion 228. The first and second buoy portions 226, 228 can be fixed relative to one another or moveable relative to one another. Further, either or both of the buoy assembly portions 226, 228 can be tuned to a selected density or specific gravity to allow for a collection area 230, defined between the two buoy portions 226, 228, to be provided at an equilibrium position that can include the selected cell population, such as the pluripotent cells from an adipose tissue sample. A syringe 240, or other appropriate collection or extraction device can be used to collect the material from within the tube 222. Appropriate separation tubes can include the GPS II™ separation system sold by Biomet, Inc. of Warsaw, Ind., USA.

Figure 11:
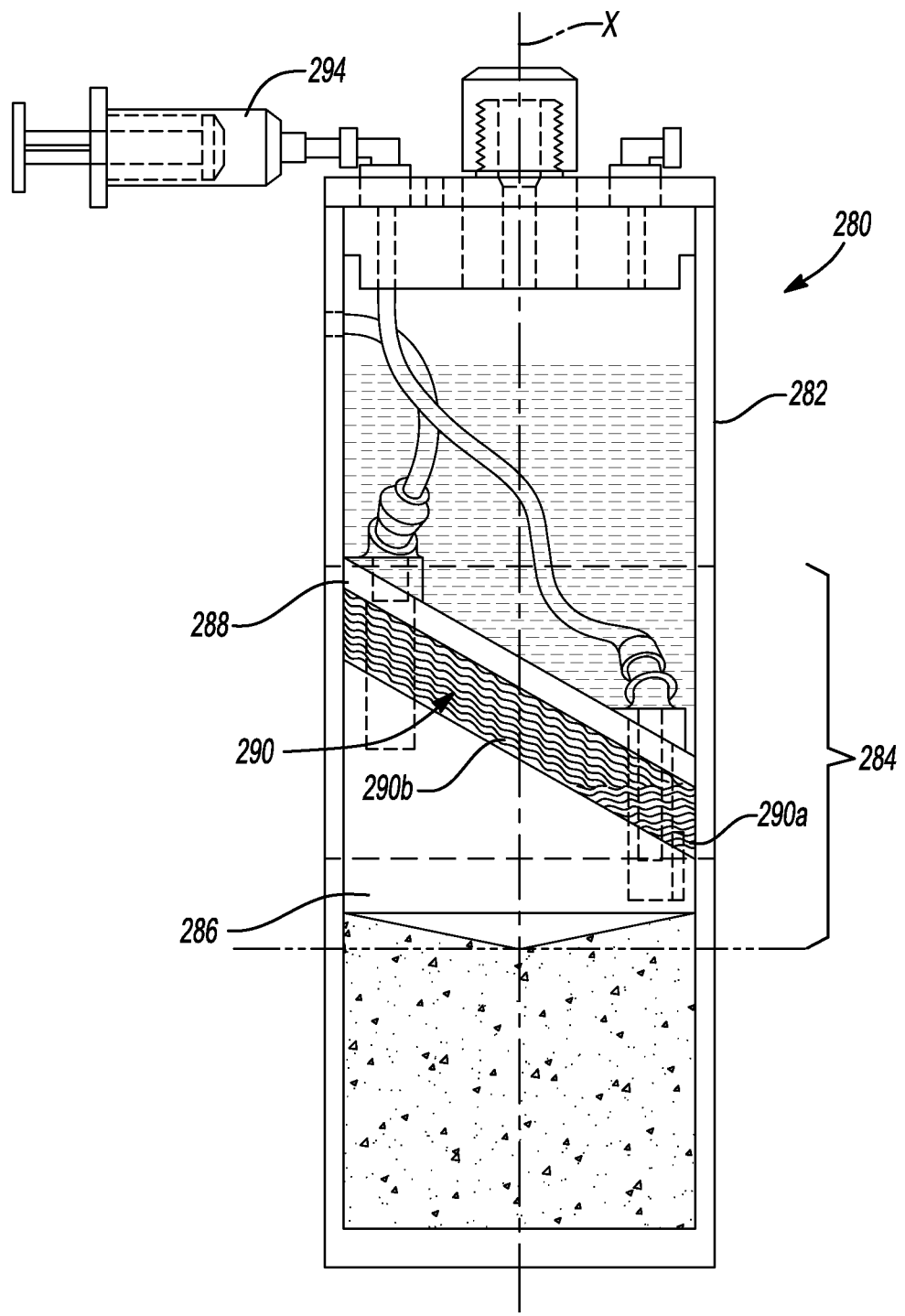
FIG. 11 is a plan view of a tissue isolator, according to various embodiments.

With reference to FIG. 11, according to various embodiments, a separation tube assembly 280 is illustrated. The separation tube assembly 280 can include a separation tube 282 that includes a separation buoy assembly 284. The buoy assembly 284 can include a main buoy portion or buoy 286 and a second buoy portion or isolator 288. The isolator 288 can be separated from the buoy portion 286 by a distance to define a collection area 290. Within the collection area 290, two or more collected materials or material areas 290a, 290b can be formed.

Again, the assembly of the buoy portion 286 and the isolator 288, or selected portions thereof, can include a tuned density or specific gravity to position the collection area 290 at a selected equilibrium position of a sample that is positioned within the tube 282. Also, an appropriate collection or extraction syringe or device 294 can be used to collect material from the tube 282. Selected separation tubes can include the GPS III™ system sold by Biomet, Inc. of Warsaw, Ind., USA. Further exemplary buoy separation systems are disclosed in U.S. patent application Ser. No. 12/101,594, filed on Apr. 11, 2008, now U.S. Pat. No. 7,806,276, issued Oct. 5, 2010, incorporated herein by reference.

It will be understood, however, that appropriate separation tubes can be designed in appropriate manners to allow for separation of a selected population from the tissue sample. Further, the separation tubes, such as the separation tubes 220, 280 can be provided with separation or power systems, such as a centrifuge system. The centrifuge system can provide a separation force or gravitational force to the sample and the buoy positioned within the tubes to allow for separation of the sample position within the tubes.

Figure 12:
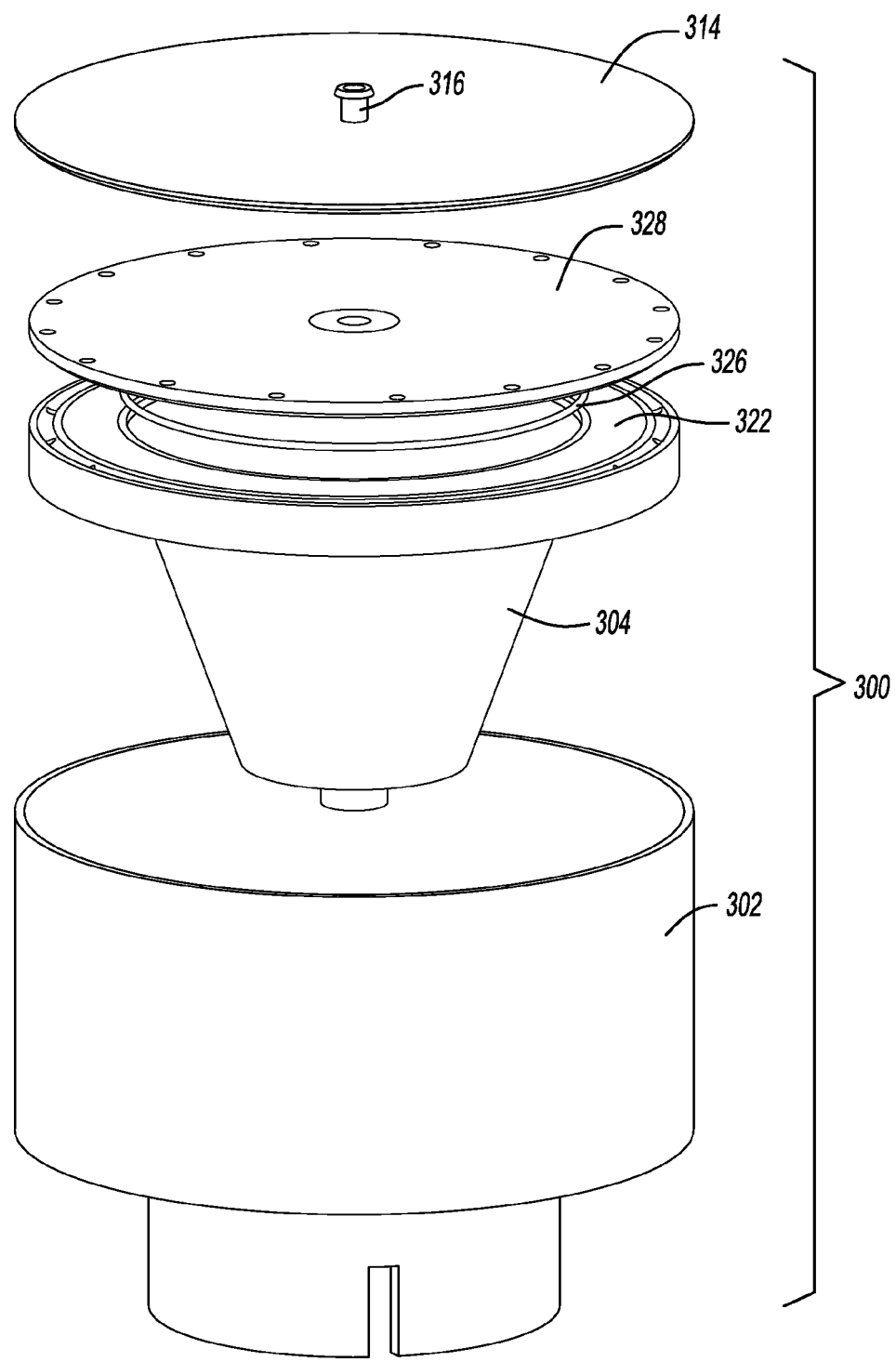
FIG. 12 is a plan perspective exploded view of a tissue isolator, according to various embodiments.
Figure 13:
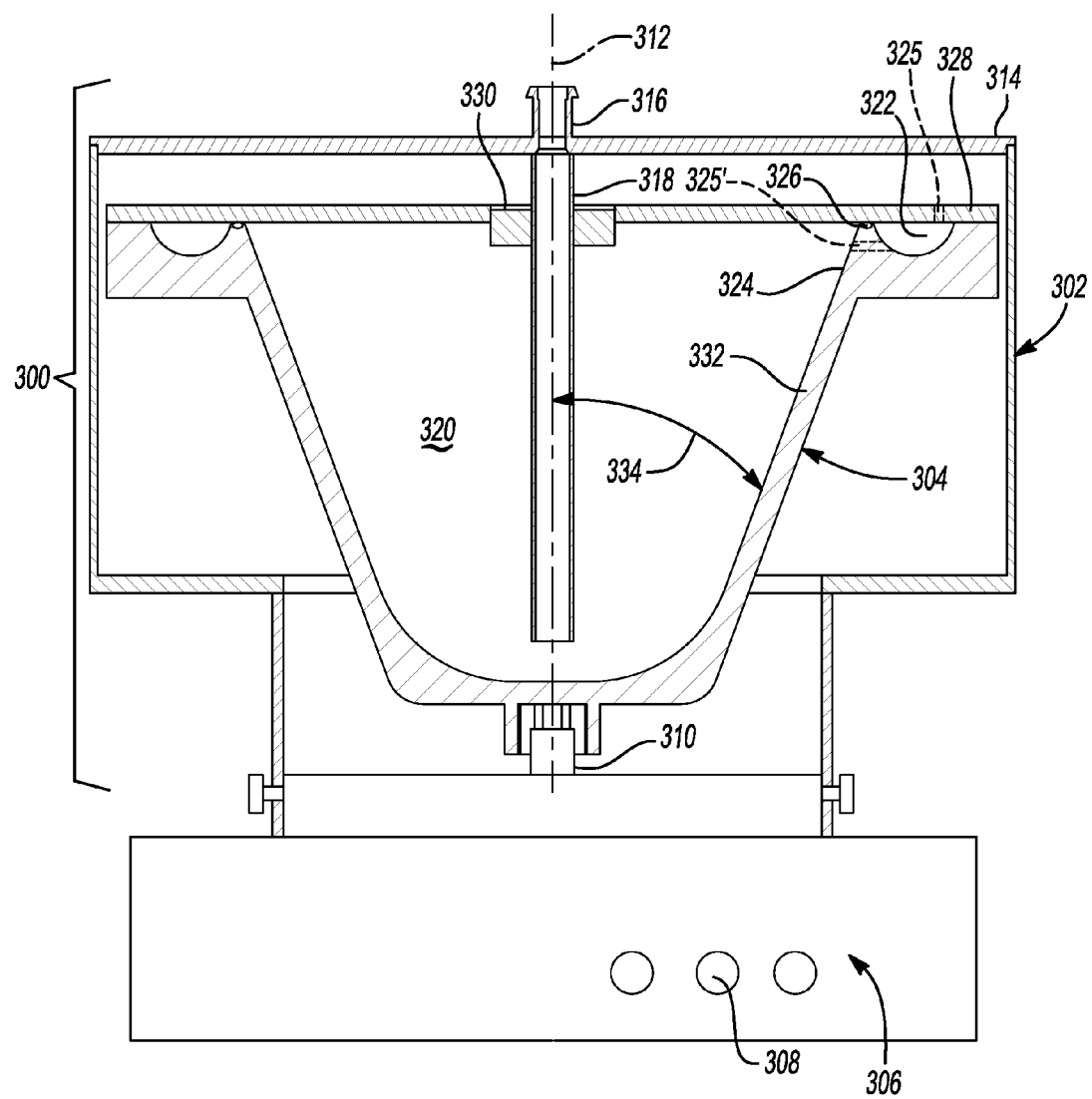
FIG. 13 is a cross-sectional view of the tissue isolator of FIG. 12.

With reference to FIGS. 12 and 13, a separation system 300 is illustrated. The separation system 300 can include three main components. The three main components can include an outer chamber or housing 302, an inner chamber or container 304, and a drive base 306. The drive base 306 can include controls 306 and an internal motor or power source to drive a rod or axle 310. The outer housing 302 can surround all or part of the drive base 308 and the axle 310. The motor base 306 can spin the inner container 304 around a central axis 312 defined by the axle 310 and a portion of the inner chamber 304. As discussed further herein, rotation around the axis 312 can cause a force within the chamber 304 to create a separation of material positioned within the chamber 304.

The outer housing 302 can engage or include a lid 314 that includes a connection or port 316. The port 316 can interconnect with a conduit or cannula 318 to allow for introduction or extraction of a material from a main container area 320 of the inner chamber 304. The main container area 320 can be used to hold a material before and during a portion of the separation in an isolation process, as discussed further herein. Further, the lid 314 may include additional ports for access to other areas of the housing 302 or the container 304, such as an isolation area, including an annular isolation ring 322.

The inner container 304 can include the main container area 320 and the isolation area 322 separated by a wall portion 324, a sealing member, such as an o-ring 326, and a lid 328. The lid 328 can be held relative to the wall portion 324 and the sealing member 326 in any appropriate manner, such as by gravity or a biasing mechanism. The lid 328 can be allowed to move relative to the central cannula 318 according to any appropriate method, such as via a bearing 330. The lid 328 can move relative to the o-ring 326 at a selected time, as discussed further herein, to allow for an opening between the main chamber area 320 and the isolation area 322. The movement of the lid 328 can be along the axis 312 or can include a movement of a portion of the lid 328 to allow for an opening between the main chamber 320 and the isolation area 322.

An optional vent 325, 325' for the isolation area 322 on the side of a barrier wall 344 (FIG. 14A) opposite an extraction port 346 (FIG. 14A) can be provided, according to various embodiments. The vent 325 can optionally open to the space above the flexible lid or liner. Alternatively, the vent 325' can optionally open to the central chamber 320. The vent 325, 325' can allow air to enter the isolation area 322 to replace the volume of material withdrawn and for air to alternately escape if the material is jetted in and out to improve cell re-suspension and recovery during material collection, such as cellular material. The vent 325, 325' can also be used as a port for introduction of a stream of wash solution. The vent 325, 325' can also include a two-way or one-way valve that is manually or automatically operated based upon pressure differentials or other mechanism.

The main chamber area 320 can include any appropriate volume or dimension. For example, a wall 332 of the main chamber area can define an angle 334 between the central axis 312 and the wall 332. The angle can be any appropriate angle, such as between about zero degrees and about ninety degrees, but generally less than ninety degrees. The angle 334 can also include about one degree to about forty degrees, and further include about ten degrees to about thirty degrees, and may also include about twenty degrees. The angle 334 can be provided or selected to assist in a separation or movement of material from the main chamber area 320 to the isolation area 322.

In addition, the inner chamber 304 can be formed of any appropriate materials, such as a material that includes a selected co-efficient of friction relative to the material positioned within the inner chamber 304 for separation. For example, an adipose tissue sample can be positioned within the inner chamber 304, such as within the inner area 320, for separation. It can be selected to include a co-efficient of friction between the adipose sample or a portion of the adipose sample to achieve a selected separation at a selected period of time and/or under a selected force, such as a centrifugal force.

Figure 14A:
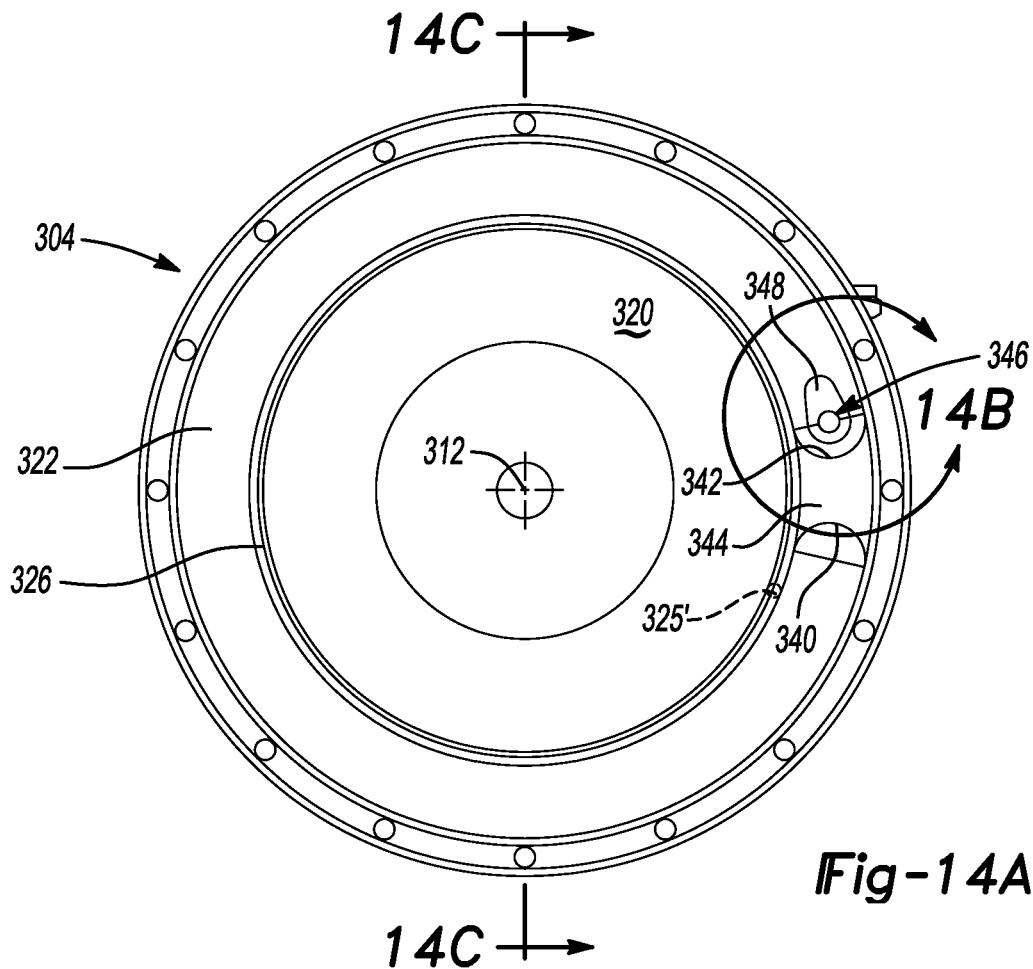
FIGS. 14A-14C are various detailed views of the tissue isolator of FIG. 12.
Figure 14B:
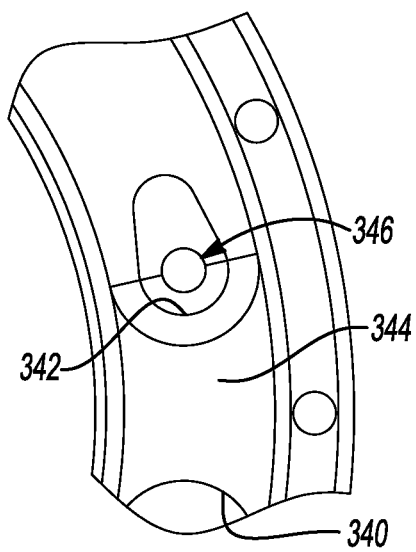
Figure 14C:
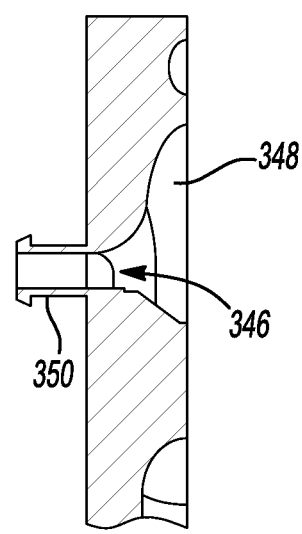

With further reference to FIGS. 14A-C, the inner chamber 304 is further illustrated. The inner chamber 304 can include the isolation area 322 separated from the main containment area 320. The isolation area 322 can include a complete or a partial annular ring surrounding the inner chamber or area 320. In addition, multiple isolation areas 322 can be provided, for example as multiple concentric annular rings (not specifically illustrated). The multiple isolation areas 322 could be used to isolate multiple fractions of intermediate or multiple densities (e.g., buffy coat from whole blood). A sealing portion or valve can be provided between each or any appropriate group of the multiple isolation areas. For example, the lid 328 or liner can include multiple regions to act as sealing portions between each of the concentric isolation areas. In this way, multiple specific and discrete materials can be separated and/or concentrated.

When a partial annular ring is provided, the isolation area 322 can extend from a first end 340 to a second end 342 that can be less than 360 degrees around the central axis 312 from the first end 340. As discussed further herein, the inclusion of the first end 340 and the second end 342 separated by a wall or barrier portion 344 can allow for substantially complete extraction of a material from the isolation area 322. Briefly, if the wall 344 were not present it may be difficult to extract material from an area not adjacent to an extraction port, such as the extraction port 346. The extraction port 346 can be positioned near or within a well or sump 348 that can further assist in removing material from the isolation area 322. The inclusion of the wall 344 allows for a vacuum to be created within the isolation area 322 relative to the extraction port 346 and allow for further extraction or efficiency of extraction from the isolation area 322.

The extraction port 346 can be accessed from any appropriate location. Examples include, through the lid 328 of the inner container 304, the lid of the exterior chamber 314, or any other area through the housing 302 or relative to the housing 302. Further, the extraction port 346 can include a cannula or connection portion 350 that extends from the port 346 and can be interconnected with any appropriate portion, such as a tube, extraction syringe, or any other appropriate mechanism. Material from the isolation area 322 can be extracted for various purposes, including those discussed further herein.

Figure 15:
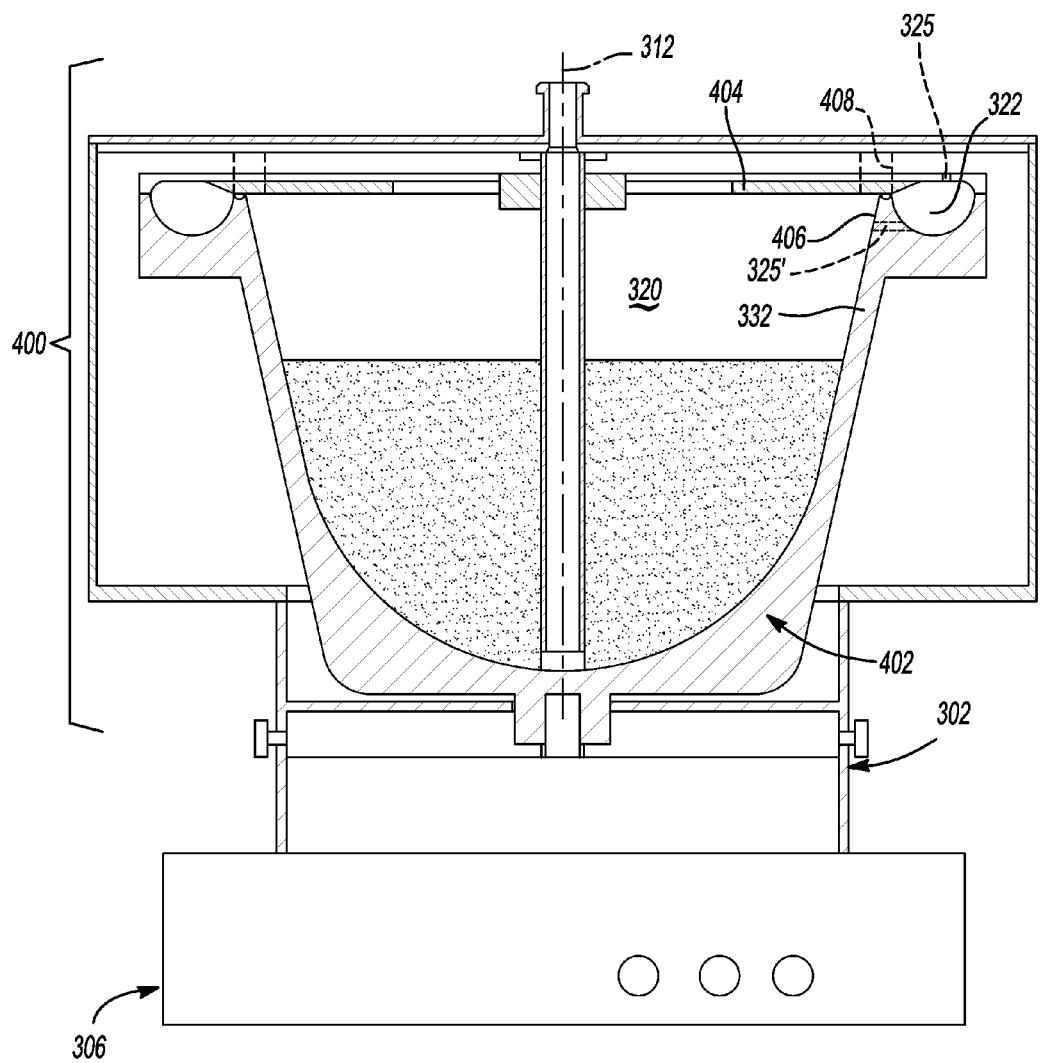
FIG. 15 is a tissue isolator, according to various embodiments.
Figure 16C:
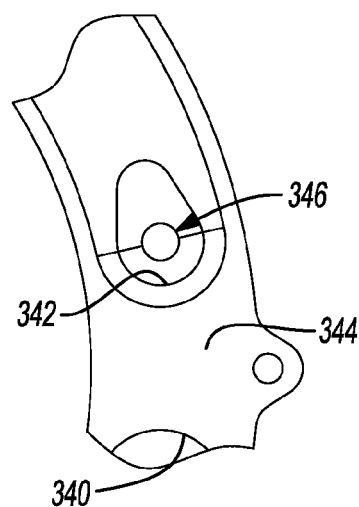
Figure 16D:
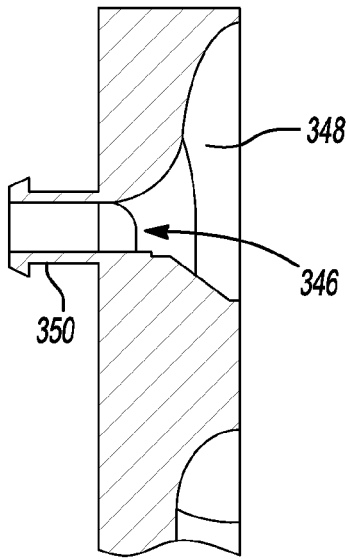

With reference to FIGS. 15 and 16 A-D, a separation assembly 400 is illustrated. The separation assembly 400 can be substantially identical to the separation assembly 300 except for various specifics of an inner chamber 402. Therefore, the outer housing 302 and the drive base 306 are simply illustrated and will not be discussed in detail here. The inner chamber 402 can also be substantially similar to the inner chamber 304. For example, the inner chamber 402 can include the central axis 312, the isolation area 322, the optional vents 325, 325', and the main inner chamber 320. Further, the various portions such as the wall 332 can be formed of similar materials and positioned at respective locations and orientations relative to other portions of the chamber 402.

The inner chamber 402, however, can differ from the inner chamber 304, illustrated in FIG. 13, at least by a lid 404 positioned relative to a wall portion 406 of the inner chamber 402. The lid portion 404 can be formed of a substantially flexible material, or a least an external or periphery portion 408 can be formed of a flexible portion. Further, the inner chamber 402 can be provided to not include the sealing member 326 provided with the inner chamber 304. The flexible portion 406 of the lid 404 can flex relative to the isolation area 322 at a selected time, as discussed further herein. Further, the flexible portion 408 of the lid 404 can also form a seal relative to the portion 324 of a wall 406. Therefore, rather than having the lid 328 that can move relative to the sealing member 326, the lid 404 can define a flexible portion 408 that can act as a sealing portion relative to the upper wall portion 406 and also flex relative to the upper wall 406. When the flexible portion 408 flexes it can provide an opening over the wall 406, thus it can act as a valve.

The lid 404 can be designed to flex at a specific location or at a specific region. It will be understood, however, that this is not necessary. The lid 404 can be provided to generally flex an appropriate amount. For example, the lid may flex at a periphery or near a center of the lid. The lid 404 can be formed of appropriate materials and of appropriate dimensions to allow the appropriate amount of flexing.

The lid 404 may also be provided as a liner over which an additional lid is provided. The additional lid or outer cover lid can provide a stop or limit to the amount of flexing or movement of the lid liner 404, under the outer lid. Accordingly, it will be understood that the lid 404 or any other appropriate flexible member can be provided to allow an escape of a selected cell fraction into the isolation area.

The inner chamber portion 402 can also define the withdrawal port 346, the sump 348, and the withdrawal cannula 350. The isolation area 322 can further include the two ends 340, 342 separated by the barrier area 344. Accordingly, the inner chamber 402 can operate substantially similar to the inner chamber 304, as discussed further herein, but can include the flexible portion 408 of the lid 404 rather than a separate and distinct sealing member, such as the sealing member 326.

Figure 17:
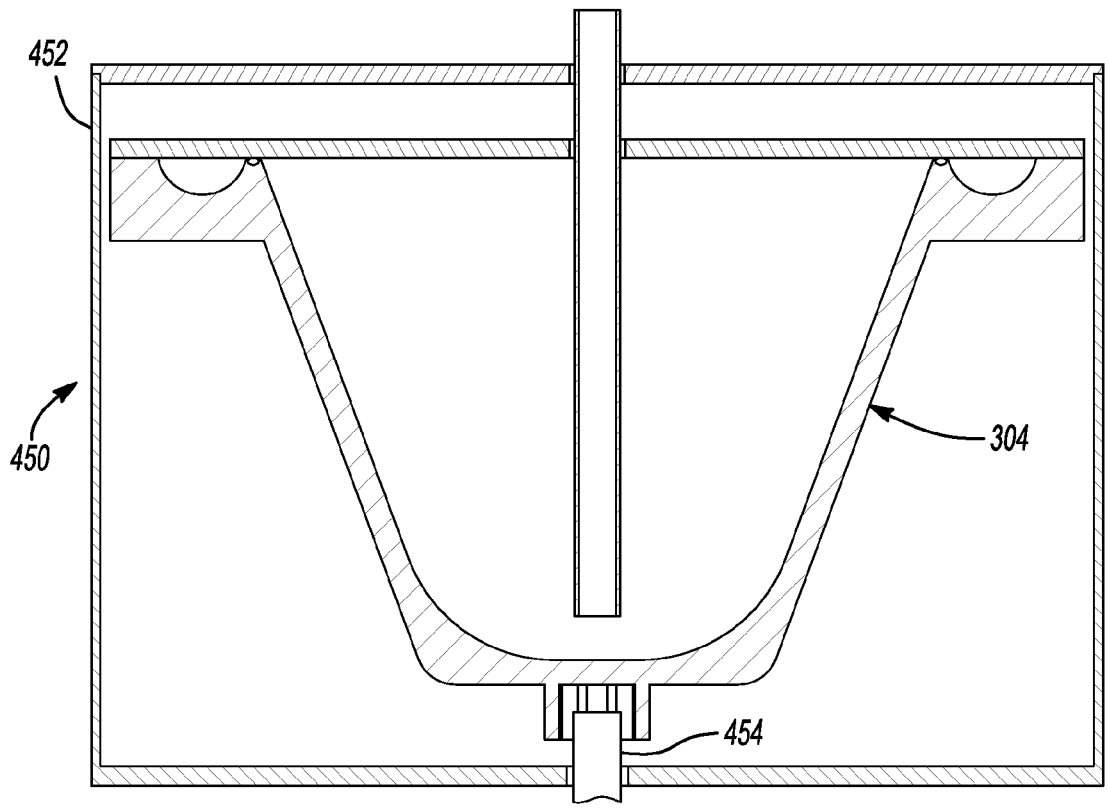
FIG. 17 is a cross-sectional view of a tissue isolator, according to various embodiments.

With reference to FIG. 17, a separation assembly 450 is illustrated. The separation assembly 450 can include an outer housing 452 that can generally include a standard centrifuge system, such as the tissue centrifuge system sold by Drucker or the CentraCL3 sold by Thermo Scientific. The centrifuge system can include a selected drive system or motor that can drive an axle or rod 454. The drive portion of the separation system 450, however, can be substantially or relatively more powerful than the drive system 306. Further, the outer housing 452 can be more robust or heavier and allow for reduced vibrations during separation and rotation of the separation inner chamber 304, or any appropriate inner chamber. The inner chamber 304 can be substantially similar to the inner chamber 402 discussed above except that it can be rotated by any appropriate motor or drive system. Therefore, the separation chamber 304 can be driven at any appropriate separation or drive speeds or for any appropriate length of time to allow for separation of a selected material.

With reference to FIGS. 18A-18G, the separation system 300 can be used to separate a selected component from a sample, such as in block 32 of FIG. 1. It will be understood that the separation system 300, however, can include various portions, either alone or in combination, such as the sealing member 326 or the flexible portion 408. Therefore, although the separation system 300 is illustrated in FIGS. 18A-18G, any appropriate separation system can be used and this is merely exemplary. Also, although the following discussion exemplary discusses separation of adipose tissue, any appropriate tissue can be separated. In addition, any appropriate cell fraction can be separated from the tissue sample.

As discussed above, a sample, such as an adipose tissue sample, can be agitated or disrupted according to various embodiments, including those discussed above. Once the tissue sample is appropriately disrupted, it can be mixed with various materials. Materials that can be mixed with the sample include citrate, a biologically acceptable acid, EDTA, or other appropriate materials. It will be further understood that a material or solution can be added at any appropriate time, such as prior to disruption of the sample, for pH adjustment, chelating, lysing, etc. It can be selected to create a solution 480 that can be placed within the main container area 320 of the inner chamber 304. The solution 480 can include the sample, such as the adipose sample, and any appropriate materials, such as citrate. The solution 480 can be adjusted to any appropriate pH and can include chelating agents, such as citrate or EDTA. Regardless it can be selected to include with the tissue sample various extra cellular materials, such as extra cellular matrix.

Various materials, however, need not be provided. For example, no extrinsic enzymes or extrinsic collagenase needs to be added to the solution 480. The disruption and the separation system can provide an appropriate separation of the tissue sample. This can also provide a final product that lacks extrinsic enzymes which can eliminate the need to attempt to remove selected enzymes. The absence of extrinsic enzymes can also eliminate concern of contamination or patient rejection. Although naturally occurring enzymes may be present in the tissue sample, which are not specifically removed, extrinsic enzymes are those added to the tissue sample whether artificially formed or not.

The sample can be placed into the inner chamber 304 in any appropriate manner, such as through the entry port 316 from a supply vessel 482. The supply vessel 482 can include the syringes, as discussed above, or any appropriate supply vessel. Further, as discussed above, the tissue sample can be provided from a patient to whom the selected material will be supplied. In various embodiments, the selected cell population can be substantially autologous. Once the solution 480 is positioned within the inner chamber 304, the drive base 306 can be activated to drive the inner chamber 304 in a selected manner, such as in a rotation around the central axis 312.

Figure 18A:
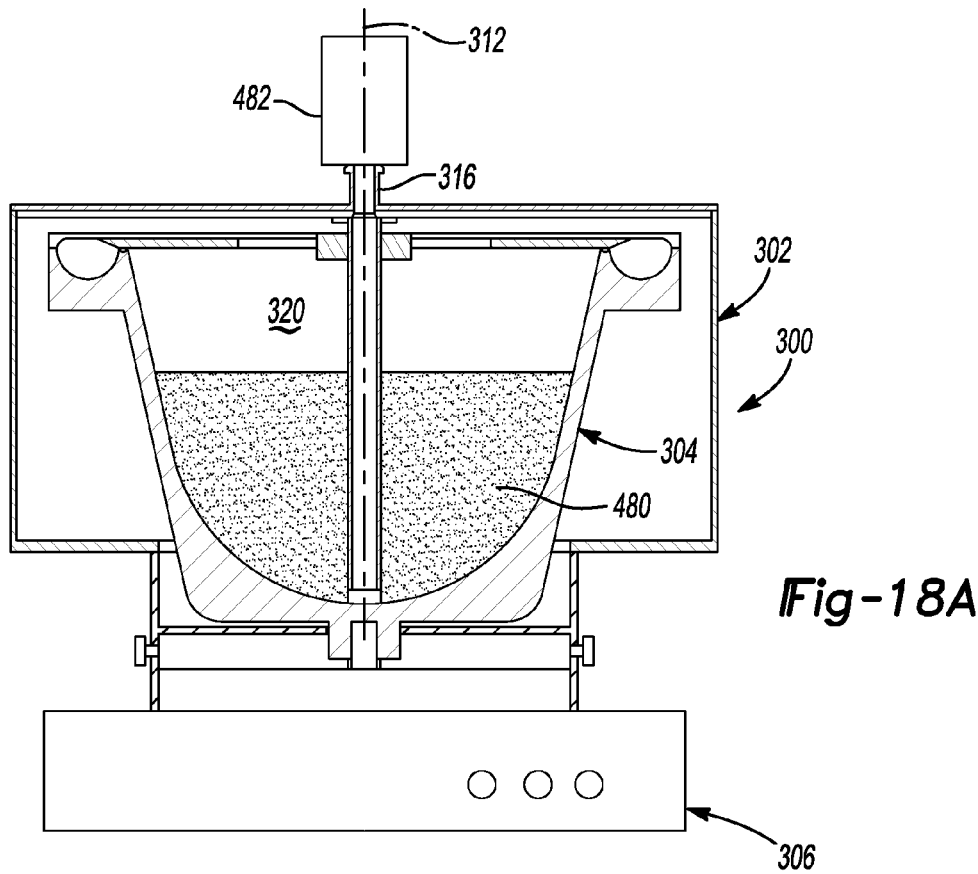
FIGS. 18A-18G illustrate a separation procedure of a tissue sample, according to various embodiments.
Figure 18B:
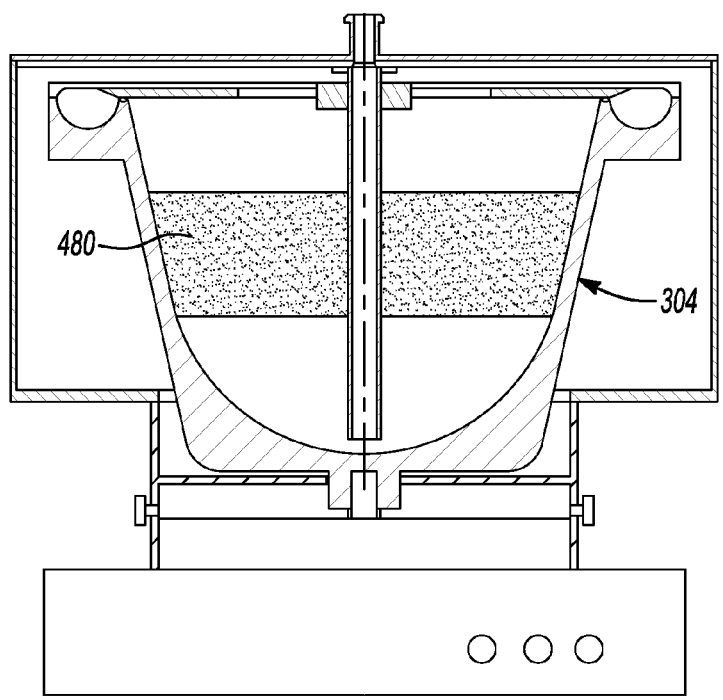
Figure 18C:
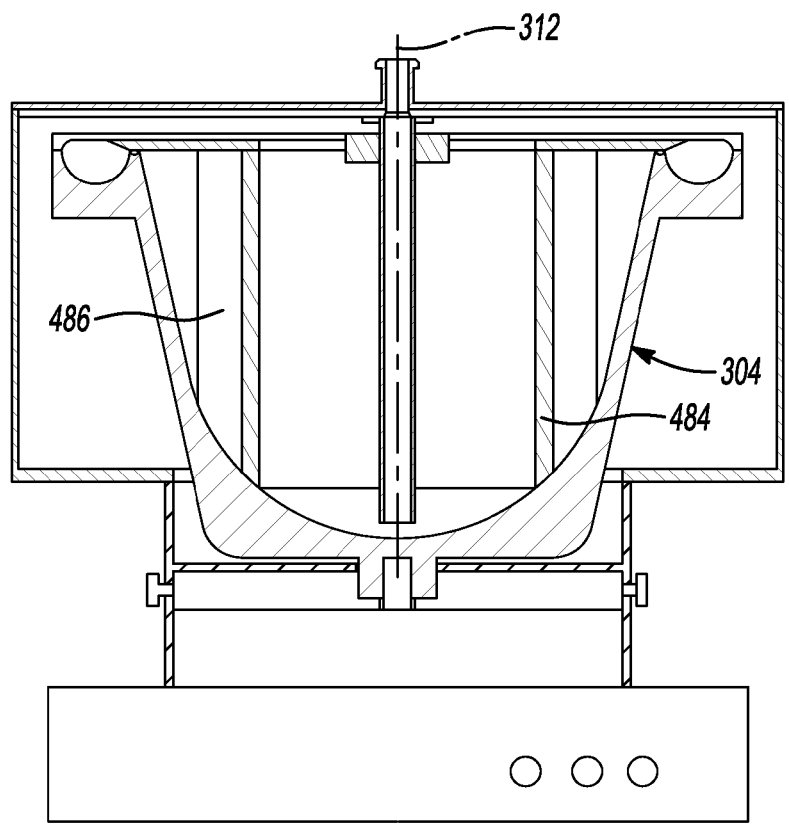
Figure 18D:
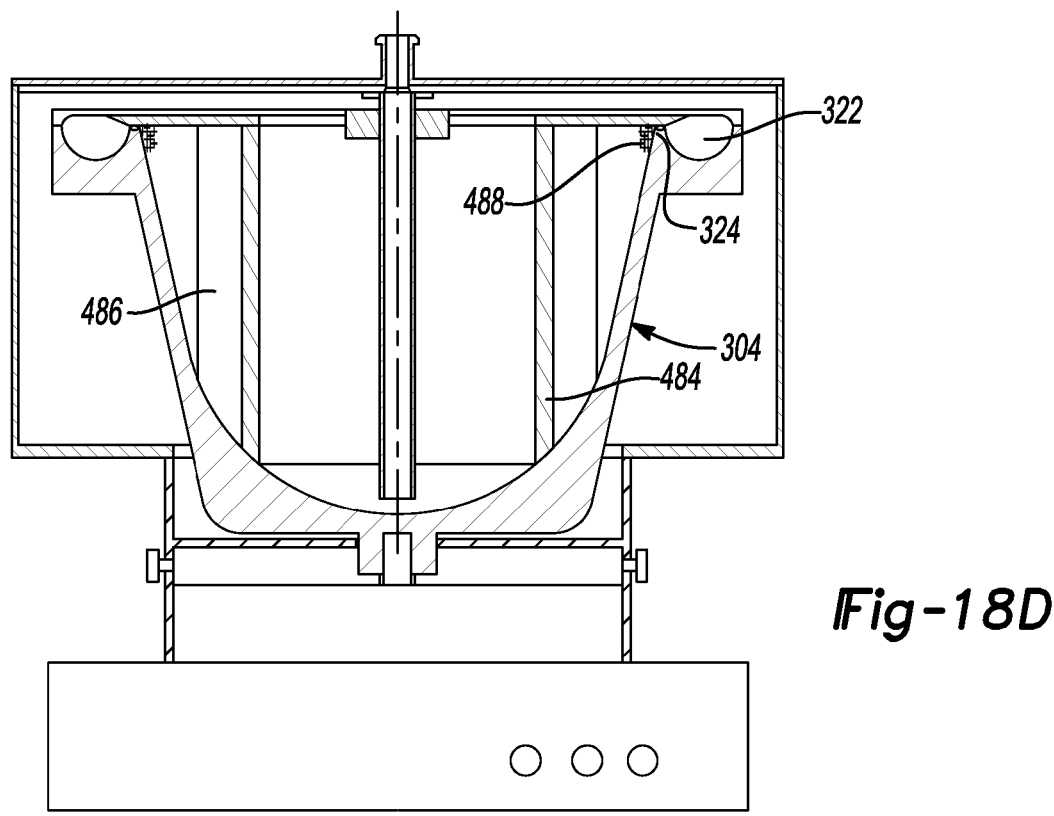

The rotation around the central axis 312 can initially cause the material to rise to a selected band within the inner chamber 304, as illustrated in FIG. 18C. The solution 480 can be moved to an appropriate location within the inner chamber 304 based upon the forces supplied with the rotation of the inner chamber 304 around the central axis 312. At a selected speed, a fat portion or oil portion 484 of the initial solution or sample can float near the central axis 312 on top of or closer to the central axis than an aqueous portion 486 of the initial sample, as illustrated in FIG. 18C. The initial separation of the fat portion 484 from the aqueous portion 486 can be achieved at a selected rotational speed or separation force. For example, the initial rotation can generate a force of about 10 to about 1000 times that of standard gravity on Earth (Gs). The rotation or centrifugation times can be any appropriate time. According to various embodiments, the rotation time can be about 60 seconds. A selected separation can occur, however, intraoperatively to allow for efficient autologous use of the selected cell fraction.

For example, a separation of the material positioned within the inner chamber 304 can be achieved through one or more spinning speeds or separation forces. Therefore, at an initial speed the fat portion 484 can be separated from the aqueous portion 486. The aqueous portion 486 can include various biological portions, such as cellular material, cellular matrix, and other appropriate materials. It will be further understood that the aqueous portion 486 can also include other materials, such as portions of whole blood, particularly if whole blood is introduced with the tissue sample in the initial solution 480.

At a selected time or after a selected period of time at a first separation force, a cellular material and/or cellular matrix (i.e. selected cell fraction) 488 can migrate to a top portion or near the seal portion 324 of the inner chamber 304. A second rotation speed or force can be about 300 Gs to about 3000 Gs. The migration of the cellular material 488 can be achieved after a selected period of rotation or at a selected rotational force. For example, a higher rotational speed or higher force can be applied to achieve a migration of the cellular material 488 towards the upper wall or the lid of the separation container 304 near the isolation annulus 322.

The separation of the selected cell fraction 488 from the remainder of the solution, including the aqueous portion 486 and the fat portion 484, can be achieved with a change in speed of rotation, a change in force, a time change in spinning of the material, or any appropriate separation. Nevertheless, once the cellular material, which can include pluripotent, multipotent, or stem cells, cellular matrix, growth factors, and other material, an isolation of the material can be achieved.

Figure 18E:
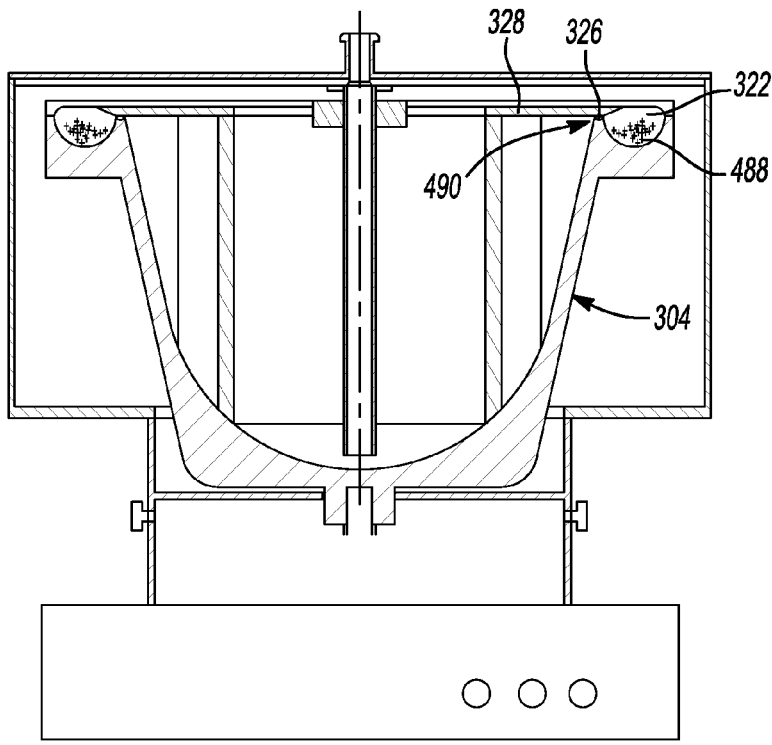
Figure 18F:
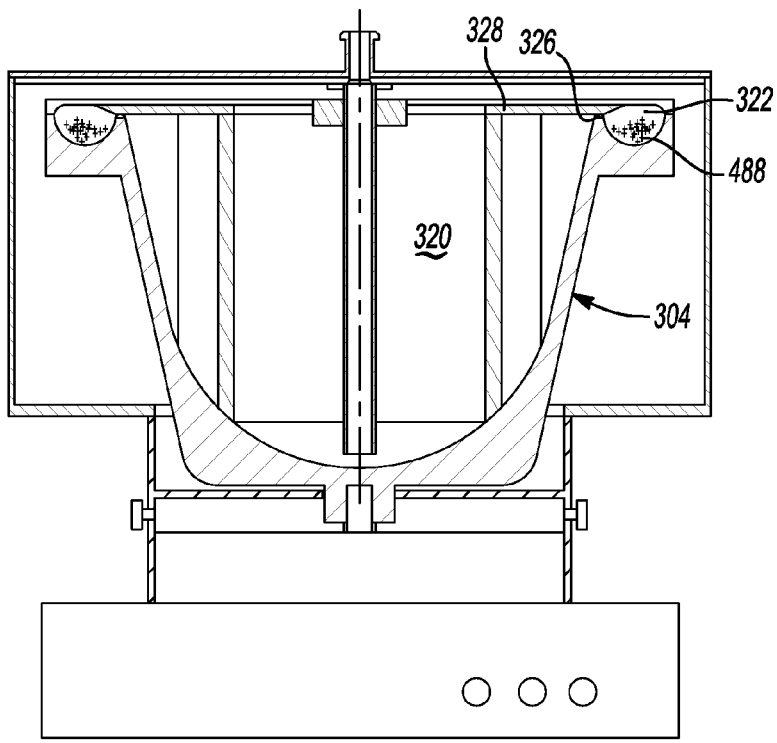

With reference to FIG. 18E, the lid 328 can move relative to the sealing member 326 to allow an opening 490 so that the cellular material 488 can be moved into the annular separation area 322. The lid 328 can move relative to the sealing member 326 for any appropriate reason. For example, electrical and/or mechanical systems can be used to open or move the lid relative to the sealing member 326. In addition, a selected force can be applied by the material within the separation chamber 320 to urge or force the lid to move or flex a selected amount opening a passage and allowing the cellular material 488 to move into the isolation area 322. For example, a third speed or force can be applied to the material within the separation chamber 304 such that it is forced against the lid 328 to move the lid relative to the sealing member 326 so that the cellular material 488 can move into the separation area 322. Therefore, the separation system 300 can allow for a substantially automatic isolation of the material based upon forces, such as centrifugal, created within the inner chamber 304, such as forces applied by the material positioned within the inner chamber 304 as created by spinning of the inner chamber 304 around the central axis 312.

If a speed is selected to achieve an opening or movement of the lid 328 relative to the sealing member 326, after a selected period of time, the speed of rotation can be changed to allow for the lid 328 to move back and engage the sealing member 326 to seal the lid onto the sealing member 326. The sealing of the lid 328 onto the sealing member 326 can substantially isolate the isolation area 322 from an area exterior to the isolation area 322, including the main separation area 320. Therefore, the isolation area 322 can be used to collect a selected material, such as cellular material, based upon a density or specific gravity of the cellular material 488 and a gravitational separation relative to the other material in the original solution 480.

Figure 18G:
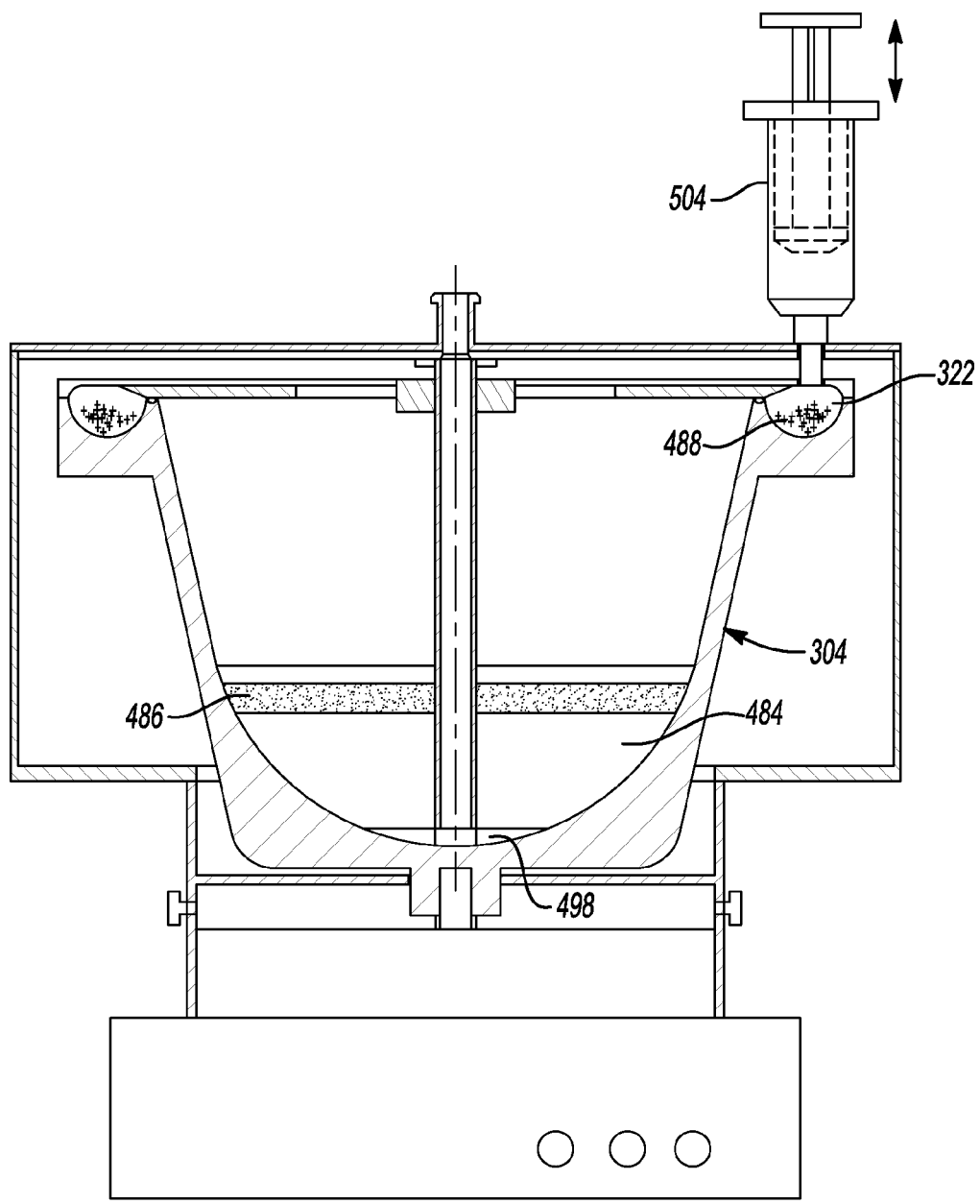

With reference to FIG. 18G, once the separation has completed, the spinning of the inner chamber 304 can be ceased for extraction of material from the inner chamber 304. The components can remain separated and may include the oil portion 484, the aqueous portion or purified fat 486, and excess or extraneous material 498. The cellular material 488, within the isolation chamber 322, can then be extracted via any appropriate extraction mechanism. For example, the selected cell fraction can be withdrawn via the extraction port or an extraction member that is positioned into the isolation area 322.

The isolation area 322 can include a barrier wall 344 to interrupt a complete annular ring of the isolation area 322. The barrier wall allows only a single path of extraction of material from the isolation area 322. The extraction port can be positioned near or at the wall 344 to allow for an efficient extraction of substantially all of the material positioned within the isolation area 322. Accordingly, a vacuum drawn at the wall 344 will urge substantially all of the material in the isolation area 322 out of the isolation area 322. It will be understood, as discussed above, that the optional vent 325, 325' can be provided to assist or allow extraction of the material from the isolation area 322.

The extraction or withdrawal of the selected cell fraction from the isolation area 322 can therefore, include various processes such as re-suspending the cellular material within a liquid material that is either positioned within the isolation area 322 from an external source or formed as a part of the separation. The re-suspension can be performed through reciprocation of an extraction syringe 500 that can form a jet of material within the isolation area 322. The formation of a jet can cause a re-suspension of the selected cell fraction 488 within the isolation area 322.

The various processes can achieve an enriched extraction of the selected cell population including stem cells, multipotent cells, or pluripotent cells from a tissue sample, such as adipose tissue. For example, the various processes, including the initial disruption to achieve a selected particle size, can allow for an efficient extraction of selected material from the tissue sample. The extraction can be efficient even without the use of extrinsic enzymes. Further, the isolation area 322 positioned relative to a main area 320 can allow for an efficient and rapid isolation of the cellular material 488 from the other material positioned within the interior chamber 304. In addition, the isolation area 322, substantially separated from other areas and forming a substantially non-continuous annular ring, can allow for re-suspension and efficient extraction of the cellular material. Therefore, the separation of the material can be both efficient and produce an extract that is highly enriched. The cell population extracted can be extracted in an appropriate and high yield from the tissue sample for various purposes. The application of the extracted cells can then be made to the patient from whom the tissue sample was acquired or to any other appropriate patient. The extracted cells can be provided for various purposes, such as healing, tissue regeneration, cell replacement therapy, scaffold seeding, cell line establishment or other uses.

According to various embodiments, the separation system and derived or separated selected cell fraction can be used to form an adipose-derived tissue implant containing pluripotent cells in a collagen extracellular matrix, comprising an extracellular matrix containing mechanically disrupted collagen substantially free of adipocytes and lipids and substantially or entirely free of extrinsic enzymes and comprised of greater than about 5% pluripotent cells. In addition, an adipose-derived tissue implant, as discussed above, can be derived where the tissue particle size is less than about 1 mm diameter. The implant may comprise blood components carried in the extracellular matrix, including growth factors and plasma, white blood cells, red blood cells, and platelets; as well as pluripotent cells carried in the extracellular matrix including fibroblasts, endothelial cells, smooth muscle cells, mast cells, pericytes, fibroblasts, lineage committed progenitor cells, and pre-adipocytes.

The pluripotent cells can be carried in the extracellular matrix, and the implant can be entirely or substantially free of extrinsic enzyme and the implant can be substantially free of adipocytes, and the isolated tissue of the pluripotent cell-containing extracellular matrix is comprised of single cells and clusters of up to about 0.10 cm in diameter. In addition, extracellular matrix may contain fragments of connective tissue, both free and associated with cells and cell clusters of diameters up to about 0.10 cm.

The adipose derived tissue implant containing pluripotent cells in a collagen extracellular matrix can be therapeutic for the various clinical indications, such as: fat transplantation for soft-tissue cosmesis, cartilage repair for either acute cartilage lesions or for osteoarthritic joints, skeletal muscle repair, cardiac muscle repair following a myocardial infarction, revascularization of critical limb ischemia, fracture repair, spine fusion, avascular necrosis, bone void fillers, augmentation of total joint arthroplasty, tendon reconstruction or repair, ligament reconstruction or repair, meniscus reconstruction or repair, wound healing or combinations thereof.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system to separate a selected cell fraction from a sample volume, comprising:
    a container having a first wall extending from a first bottom wall to a an upper rim having an interior surface and an exterior surface;
    a collection section positioned near the upper rim and at least contacting the exterior surface of the first wall, the collection section having a second wall extending from a second bottom wall to the upper rim, and wherein the second bottom wall is nearer the upper rim than the first bottom wall;
    a lid assembly extending over both the container and the collection section;
    a sealing section operable to seal a collection volume within the collection section from a container volume in the container;
    a flexible section operable to allow the sealing section to move between an open position and a closed position; and
    a drive motor operable to rotate the container and the collection section simultaneously;
    wherein in the closed position the sealing section selectively seals the collection volume from the container volume;
    wherein at a selected spin rate the sealing section moves to the open position from the closed position.

2. The system of claim 1, further comprising:
    a sealing member positioned in an annular depression surrounding the container and positioned at the upper rim;
    wherein the sealing section contacts the sealing member to seal collection volume from the container volume.

3. The system of claim 2, wherein the disruption system includes a perforated member defining at least a through bore;
 a sample containing volume having an end covered by the perforated member; and
 a forcing member operable to force the sample volume through the perforated member to achieve a sample particle.

4. The system of claim 1, further comprising:
 a disruption system operable to form a sample particle from a sample volume.

5. The system of claim 4, wherein the disruption system is operable to form a sample particle having an average particle size in a range of about 0.1 mm to about 5 mm.

6. The system of claim 4, wherein the disruption system is operable to form a sample particle having an average particle size in a range of about 0.5 mm to about 2 mm.

7. The system of claim 4, wherein the disruption system is operable to form a sample particle having an average particle size of about 1 mm.

8. The system of claim 1, further comprising:
 a housing operable to enclose all of the container, the collection section, the lid, the sealing section, the flexible section, and the drive motor.

9. The system of claim 1, further comprising:
 an outer housing operable to contain the container, the collection section, the lid, the sealing section, and the flexible section; and
 a drive base operable to contain the drive motor;
 wherein the outer housing is removeably attachable to the drive base.

10. The system of claim 1, wherein the collection section defines an annular well surrounding the container;
 a barrier wall defining a first end and a second end of a collection section, wherein the barrier wall disrupts the complete annular well of the collection section;
 wherein a vacuum is operable to be formed near the first end of the collection section to draw substantially all material out of the collection section through a port.

11. The system of claim 1, wherein the flexible section is formed by a portion of the lid assembly and a portion of the flexible section forms the sealing section, wherein the flexible section is configured to flex to provide an opening between the collection volume and the container volume.

12. The system of claim 1, where the lid assembly includes a first flexible lid forming the flexible section and sealing section and a second lid positioned atop the first flexible lid.

13. A system to separate a selected cell fraction from a sample volume, comprising:
 a container having a main container area and an isolation area spaced from the main container area with a wall portion therebetween; and
 a lid covering both the main container area and the isolation area, the lid including,
  a sealing portion operable to seal the main container area from the isolation area, and
  a flexible portion operable to allow the sealing portion to move between an open position and a closed position,
  wherein in the closed position the sealing position seals the main container area from the isolation area and in the open position the isolation area is opened to the main container area.

14. The system of claim 13, further comprising an outer housing, wherein the container having the main container area and the isolation area are contained within the outer housing.

15. The system of claim 14, further comprising a drive base having a drive motor, the drive base being coupled to the outer housing and the container to rotate the container about a central axis.

16. The system of claim 13, wherein the isolation area is an annular well surrounding the main container area, where the isolation area includes a barrier wall extending a width of the isolation area, where the barrier wall defines a first end and a second end of the isolation area.

17. The system of claim 13, wherein a portion of the flexible portion of the lid forms the sealing portion.

18. The system of claim 17, further comprising an outer covering lid positioned atop the lid, wherein the outer covering lid provides a limit to the amount of flexing of the lid.

19. A system to separate a selected cell fraction from a sample volume, comprising:
 a container having a main container area and an isolation area spaced from the main container area with a wall portion therebetween, the isolation area forming an annular well around the main container area;
 a barrier wall extending a width of the isolation area, where the barrier wall defines a first end and a second end of the isolation area; and
 a lid covering both the main container area and the isolation area, the lid including,
  a sealing portion operable to seal the main container area from the isolation area, and
  a flexible portion operable to allow the sealing portion to move between an open position and a closed position,
  wherein in the closed position the sealing portion seals the main container area from the isolation area and in the open position the main container area is open to the isolation area.

20. The system of claim 19, further comprising an outer covered lid positioned atop the lid, wherein the outer covered lid provides a limit to the amount of flexing of the lid.

21. The system of claim 19, wherein the annular well includes a sump defined within the annular well and a port positioned relative to the sump, wherein the selected cell fraction is operable to collect within the sump defined within the isolation area and a suction force can be applied at the first end to move the selected cell fraction within the isolation area.

22. The system of claim 19, further comprising a drive motor operable to rotate the container about a central axis, wherein at a selected spin rate the lid is operable to flex at a periphery with the flexible portion to move the sealing portion from the closed position to the open position.

* * * * *